US012721801B2

(12) United States Patent
Widgerow et al.

(10) Patent No.: US 12,721,801 B2
(45) **Date of Patent: *Sep. 1, 2026**

(54) COMPOSITIONS AND METHODS RELATING TO STIMULATION OF HYALURONIC ACID

(71) Applicant: Alastin Skincare, Inc., Carlsbad, CA (US)

(72) Inventors: Alan David Widgerow, Carlsbad, CA (US); John A. Garruto, Carlsbad, CA (US)

(73) Assignee: Alastin Skincare, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/064,198

(22) Filed: Feb. 26, 2025

(65) Prior Publication Data

US 2026/0083656 A1 Mar. 26, 2026

Related U.S. Application Data

(63) Continuation of application No. 18/297,422, filed on Apr. 7, 2023, which is a continuation of application No. PCT/US2021/054010, filed on Oct. 7, 2021.

(60) Provisional application No. 63/218,068, filed on Jul. 2, 2021, provisional application No. 63/089,424, filed on Oct. 8, 2020.

(51) Int. Cl.

| | |
|---|---|
| ***A61K 8/64*** | (2006.01) |
| ***A61G 19/00*** | (2006.01) |
| ***A61K 8/35*** | (2006.01) |
| ***A61K 8/55*** | (2006.01) |
| ***A61K 8/73*** | (2006.01) |
| ***A61K 8/9728*** | (2017.01) |
| ***A61K 36/07*** | (2006.01) |
| ***A61Q 19/00*** | (2006.01) |
| ***C07K 7/06*** | (2006.01) |

(52) U.S. Cl.

CPC ................ *A61K 8/64* (2013.01); *A61G 19/00* (2013.01); *A61K 8/35* (2013.01); *A61K 8/553* (2013.01); *A61K 8/735* (2013.01); *A61K 8/9728* (2017.08); *A61K 36/07* (2013.01); *C07K 7/06* (2013.01); *A61K 2800/10* (2013.01); *A61K 2800/78* (2013.01)

(58) Field of Classification Search

None

See application file for complete search history.

(56) References Cited

U.S. PATENT DOCUMENTS

| | | | |
|---|---|---|---|
| 2009/0054349 A1 | 2/2009 | Chung et al. | |
| 2010/0215726 A1 | 8/2010 | Roth | |
| 2011/0015120 A1 | 1/2011 | Bortolin | |
| 2012/0288478 A1* | 11/2012 | Florence | A61K 8/42 424/93.1 |
| 2013/0078294 A1 | 3/2013 | Alexiades-Armenakas | |
| 2013/0330335 A1 | 12/2013 | Bremel et al. | |
| 2014/0141044 A1 | 5/2014 | Bhatt et al. | |
| 2016/0075738 A1 | 3/2016 | Ferrer Montiel et al. | |
| 2019/0262418 A1 | 8/2019 | Garruto et al. | |

FOREIGN PATENT DOCUMENTS

| | | |
|---|---|---|
| CN | 109528612 A | 3/2019 |
| CN | 110833516 A | 2/2020 |

OTHER PUBLICATIONS

National Center for Biotechnology Information. "PubChem Compound Summary for CID 73587, glycyl-L-histidyl-L-lysine" PubChem, https://pubchem.ncbi.nlm.nih.gov/compound/73587. Accessed Feb. 9, 2026, 2026. (Year: 2026).*

National Center for Biotechnology Information. "PubChem Compound Summary for CID 24998056, Hexapeptide-11" PubChem, https://pubchem.ncbi.nlm.nih.gov/compound/Hexapeptide-11. Accessed Feb. 9, 2026, 2026. (Year: 2026).*

National Center for Biotechnology Information. "PubChem Compound Summary for CID 10097423, Hexapeptide-12" PubChem, https://pubchem.ncbi.nlm.nih.gov/compound/10097423. Accessed Feb. 9, 2026, 2026. (Year: 2026).*

National Center for Biotechnology Information. "PubChem Compound Summary for CID 12934, Valyl-glycyl-valyl-alanyl-prolyl-glycine" PubChem, https://pubchem.ncbi.nlm.nih.gov/compound/124934. Accessed Feb. 9, 2026, 2026. (Year: 2026).*

Errante et al. (Cosmeceutical Peptides in the Framework of Sustainable Wellness Economy. Front. Chem. 2020, 8, 572923 (Year: 2020).*

Bai et al., "Functional overlap of the *Arabidopsis* leaf and root microbiota", Nature, vol. 528, No. 7582, Dec. 17, 2015, pp. 364-369.

Database GNPD [Online] Mintel; Mar. 14, 2019 (Mar. 14, 2019), anonymous: "Lift & Firm Moisturizer", XP093165177, Database accession No. 6377319.

Garrido-Oter et al., "Direct Submission", Institute of Microbiology, ETH Zurich, Oct. 8, 2015, Retrieved from the Internet: https://www.ncbi.nlm.nih.gov/protein/945271648.

International Preliminary Report on Patentability on PCT Appl. Ser. No. PCT/US2021/054010 dated Apr. 20, 2023 (10 pages).

International Search Report and Written Opinion issued in PCT Application No. PCT/US2021/054010 dated Mar. 1, 2022 (14 pages).

* cited by examiner

*Primary Examiner* — Christina Bradley

(74) *Attorney, Agent, or Firm* — Sunit Talapatra; Foley & Lardner LLP

(57) ABSTRACT

Compositions and methods for stimulating intrinsic hyaluronic acid production are provided herein. Compositions and methods for stimulating intrinsic hyaluronic acid production can improve skin moisture and elasticity.

20 Claims, 6 Drawing Sheets

Specification includes a Sequence Listing.

COMPOSITIONS AND METHODS RELATING TO STIMULATION OF HYALURONIC ACID

CROSS-REFERENCE

This application is a continuation of U.S. patent application Ser. No. 18/297,422 filed Apr. 7, 2023, which is a continuation application of International (PCT) Application No. PCT/US2021/054010 filed Oct. 7, 2021, which application claims the benefit of (i) U.S. Provisional Patent Application No. 63/089,424 filed on Oct. 8, 2020; and (ii) U.S. Provisional Patent Application No. 63/218,068 filed on Jul. 2, 2021, all of which are incorporated by reference in their entireties.

SEQUENCE LISTING

The instant application contains a Sequence Listing which has been submitted electronically in XML format and is hereby incorporated by reference in its entirety. Said XML copy, created on Aug. 1, 2025, is named 105153-50713_SL.xml and is 31,402 bytes in size.

BACKGROUND

Hyaluronic acid is a nonsulfated glycosaminoglycan that is distributed widely throughout connective, epithelial, and neural tissues such as the skin. Hyaluronic acid has been used in topical compositions for the skin because of its ability to promote skin hydration. However, low molecular weight hyaluronic acid can promote the production of proinflammatory mediators. Thus, there exists a need to provide topical compositions that promote intrinsic hyaluronic acid production without the negative effects such as the production of proinflammatory mediators.

BRIEF SUMMARY

The skin contains 50% of the body's hyaluronic acid (HA). HA is a major component of the extracellular matrix (ECM) of the skin, appearing in epidermis, dermis, and the basal lamina that lies between. HA is also observed intracellularly and plays an important role in metabolism, cell turnover, differentiation, cell movement, tissue repair, hydration, nutrient exchange, and protection against free radical damage. The rapid turnover of HA suggests that HA may also be important as a conduit for the removal of toxic materials. Native HA as well as modified cross-linked HA has been employed to help skin maintain and even regain elasticity, turgor, as well as moisture. Topical compositions are needed to promote intrinsic HA stimulation in the skin.

An aspect described herein is a topical composition for stimulating hyaluronic acid comprising: a synthetic tripeptide; an octapeptide; and a hexapeptide, wherein the topical composition stimulates hyaluronic acid. In one feature, the synthetic tripeptide comprises tetradecyl-diaminobutyroyl-valyldiaminobutyric urea trifluoroacetate. In one feature, the octapeptide is encapsulated in a liposome. In one feature, the octapeptide comprises an amino acid sequence GDGDGASA (SEQ ID NO: 1), GPMGPSGP (SEQ ID NO: 2), GLGPGARA (SEQ ID NO: 3), GPQGFQGP (SEQ ID NO: 4), GPHGVREA (SEQ ID NO: 5), GPMGPRGP (SEQ ID NO: 6), GPGKNGDD (SEQ ID NO: 7), or GPMGPRGP (SEQ ID NO: 8). In one feature, the octapeptide comprises an amino acid sequence GDGDGASA (SEQ ID NO: 1). In one feature, the octapeptide comprises an amino acid sequence GPMGPSGP (SEQ ID NO: 2). In one feature, the octapeptide comprises an amino acid sequence GLGPGARA (SEQ ID NO: 3). In one feature, the octapeptide comprises an amino acid sequence GPQGFQGP (SEQ ID NO: 4). In one feature, the octapeptide comprises an amino acid sequence GPHGVREA (SEQ ID NO: 5). In one feature, the octapeptide comprises an amino acid sequence GPMGPRGP (SEQ ID NO: 6). In one feature, the octapeptide comprises an amino acid sequence GPGKNGDD (SEQ ID NO: 7). In one feature, the octapeptide comprises an amino acid sequence GPMGPRGP (SEQ ID NO: 8). In one feature, the hexapeptide is hexapeptide-11. In one feature, the hexapeptide-11 is encapsulated in a liposome. In one feature, the topical composition further comprises lactoferrin. In one feature, the lactoferrin is encapsulated in a liposome. In one feature, the topical composition further comprises phosphatidylserine. In one feature, the topical composition further comprises Tremella fuciformis extract. In one feature, the topical composition further comprises sodium hyaluronate crosspolymer. In one feature, the topical composition further comprises hydroxymethoxyphenyl decanone. In one feature, the topical composition is aqueous. In one feature, the octapeptide comprises an amino acid sequence GPMGPSGP (SEQ ID NO: 2) and the hexapeptide is hexapeptide-11. In one feature, the topical composition further comprises lactoferrin, phosphatidylserine, Tremella fuciformis extract, sodium hyaluronate crosspolymer, hydroxymethoxyphenyl decanone, or combinations thereof. In one feature, the octapeptide comprises an amino acid sequence GLGPGARA (SEQ ID NO: 3) and the hexapeptide is hexapeptide-11. In one feature, the topical composition further comprises lactoferrin, phosphatidylserine, Tremella fuciformis extract, sodium hyaluronate crosspolymer, hydroxymethoxyphenyl decanone, or combinations thereof. In one feature, the octapeptide comprises an amino acid sequence GPQGFQGP (SEQ ID NO: 4) and the hexapeptide is hexapeptide-11. In one feature, the topical composition further comprises lactoferrin, phosphatidylserine, Tremella fuciformis extract, sodium hyaluronate crosspolymer, hydroxymethoxyphenyl decanone, or combinations thereof. In one feature, the octapeptide comprises an amino acid sequence GPHGVREA (SEQ ID NO: 5) and the hexapeptide is hexapeptide-11. In one feature, the topical composition further comprises lactoferrin, phosphatidylserine, Tremella fuciformis extract, sodium hyaluronate crosspolymer, hydroxymethoxyphenyl decanone, or combinations thereof. In one feature, the octapeptide comprises an amino acid sequence GPMGPRGP (SEQ ID NO: 6) and the hexapeptide is hexapeptide-11. In one feature, the topical composition further comprises lactoferrin, phosphatidylserine, Tremella fuciformis extract, sodium hyaluronate crosspolymer, hydroxymethoxyphenyl decanone, or combinations thereof. In one feature, the octapeptide comprises an amino acid sequence GPGKNGDD (SEQ ID NO: 7) and the hexapeptide is hexapeptide-11. In one feature, the topical composition further comprises lactoferrin, phosphatidylserine, Tremella fuciformis extract, sodium hyaluronate crosspolymer, hydroxymethoxyphenyl decanone, or combinations thereof. In one feature, the octapeptide comprises an amino acid sequence GPMGPRGP (SEQ ID NO: 8) and the hexapeptide is hexapeptide-11. In one feature, the topical composition further comprises lactoferrin, phosphatidylserine, Tremella fuciformis extract, sodium hyaluronate crosspolymer, hydroxymethoxyphenyl decanone, or combinations thereof.

An aspect described herein is a method for stimulating hyaluronic acid production, comprising administering a topical composition comprising: a synthetic tripeptide; an octapeptide; and a hexapeptide. In one feature, the synthetic tripeptide comprises tetradecyl-diaminobutyroylvalyl-diaminobutyric urea trifluoroacetate. In one feature, the octapeptide is encapsulated in a liposome. In one feature, the octapeptide comprises an amino acid sequence GDGD-GASA (SEQ ID NO: 1), GPMGPSGP (SEQ ID NO: 2), GLGPGARA (SEQ ID NO: 3), GPQGFQGP (SEQ ID NO: 4), GPHGVREA (SEQ ID NO: 5), GPMGPRGP (SEQ ID NO: 6), GPGKNGDD (SEQ ID NO: 7), or GPMGPRGP (SEQ ID NO: 8). In one feature, the octapeptide comprises an amino acid sequence GDGDGASA (SEQ ID NO: 1). In one feature, the octapeptide comprises an amino acid sequence GPMGPSGP (SEQ ID NO: 2). In one feature, the octapeptide comprises an amino acid sequence GLGP-GARA (SEQ ID NO: 3). In one feature, the octapeptide comprises an amino acid sequence GPQGFQGP (SEQ ID NO: 4). In one feature, the octapeptide comprises an amino acid sequence GPHGVREA (SEQ ID NO: 5). In one feature, the octapeptide comprises an amino acid sequence GPMGPRGP (SEQ ID NO: 6). In one feature, the octapeptide comprises an amino acid sequence GPGKNGDD (SEQ ID NO: 7). In one feature, the octapeptide comprises an amino acid sequence GPMGPRGP (SEQ ID NO: 8). In one feature, the hexapeptide is hexapeptide-11. In one feature, the hexapeptide-11 is encapsulated in a liposome. In one feature, the topical composition further comprises lactoferrin. In one feature, the lactoferrin is encapsulated in a liposome. In one feature, the topical composition further comprises phosphatidylserine. In one feature, the topical composition further comprises Tremella fuciformis extract. In one feature, the topical composition further comprises sodium hyaluronate crosspolymer. In one feature, the topical composition further comprises hydroxymethoxyphenyl decanone. In one feature, the octapeptide comprises an amino acid sequence GPMGPSGP (SEQ ID NO: 2) and the hexapeptide is hexapeptide-11. In one feature, the topical composition further comprises lactoferrin, phosphatidylserine, Tremella fuciformis extract, sodium hyaluronate crosspolymer, hydroxymethoxyphenyl decanone, or combinations thereof. In one feature, the octapeptide comprises an amino acid sequence GLGPGARA (SEQ ID NO: 3) and the hexapeptide is hexapeptide-11. In one feature, the topical composition further comprises lactoferrin, phosphatidylserine, Tremella fuciformis extract, sodium hyaluronate crosspolymer, hydroxymethoxyphenyl decanone, or combinations thereof. In one feature, the octapeptide comprises an amino acid sequence GPQGFQGP (SEQ ID NO: 4) and the hexapeptide is hexapeptide-11. In one feature, the topical composition further comprises lactoferrin, phosphatidylserine, Tremella fuciformis extract, sodium hyaluronate crosspolymer, hydroxymethoxyphenyl decanone, or combinations thereof. In one feature, the octapeptide comprises an amino acid sequence GPHGVREA (SEQ ID NO: 5) and the hexapeptide is hexapeptide-11. In one feature, the topical composition further comprises lactoferrin, phosphatidylserine, Tremella fuciformis extract, sodium hyaluronate crosspolymer, hydroxymethoxyphenyl decanone, or combinations thereof. In one feature, the octapeptide comprises an amino acid sequence GPMGPRGP (SEQ ID NO: 6) and the hexapeptide is hexapeptide-11. In one feature, the topical composition further comprises lactoferrin, phosphatidylserine, Tremella fuciformis extract, sodium hyaluronate crosspolymer, hydroxymethoxyphenyl decanone, or combinations thereof. In one feature, the octapeptide comprises an amino acid sequence GPGKNGDD (SEQ ID NO: 7) and the hexapeptide is hexapeptide-11. In one feature, the topical composition further comprises lactoferrin, phosphatidylserine, Tremella fuciformis extract, sodium hyaluronate crosspolymer, hydroxymethoxyphenyl decanone, or combinations thereof. In one feature, the octapeptide comprises an amino acid sequence GPMGPRGP (SEQ ID NO: 8) and the hexapeptide is hexapeptide-11. In one feature, the topical composition further comprises lactoferrin, phosphatidylserine, Tremella fuciformis extract, sodium hyaluronate crosspolymer, hydroxymethoxyphenyl decanone, or combinations thereof. In one feature, the topical composition is aqueous. In one feature, the topical composition improves skin moisture. In one feature, the topical composition reduces appearance of a bruise, an aging spot, or a wrinkle. In one feature, the topical composition is administered 1, 2, 3, 4, 5, 6, 7, or 8 times a day. In one feature, the individual is a human.

INCORPORATION BY REFERENCE

Figure 1:
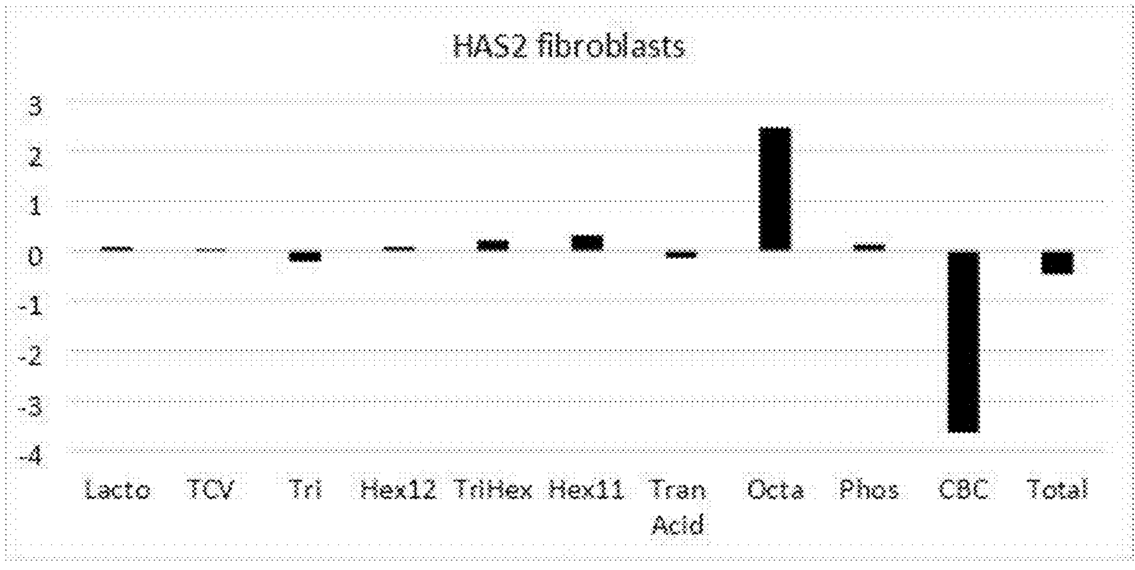
FIG. 1 depicts a graph of Hyaluronic acid Synthase 2 (HAS2) expression in fibroblasts.

All publications, patents, and patent applications mentioned in this specification are herein incorporated by reference to the same extent as if each individual publication, patent, or patent application was specifically and individually indicated to be incorporated by reference.

DETAILED DESCRIPTION

Definitions

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

Compositions

Hyaluronic acid (HA) is a major component of the extracellular matrix (ECM) of the skin. HA plays an important role in metabolism, cell turnover, differentiation, cell movement, tissue repair, hydration, nutrient exchange, and protection against free radical damage. Topical compositions are needed to promote intrinsic HA stimulation in the skin.

Described herein are compositions and methods for stimulation hyaluronic acid (HA). Compositions and methods as described herein may comprise HA such as high molecular weight HA. Compositions and methods as described herein may further comprise one or more agents that stimulate cells in the skin to produce more HA. Compositions and methods as described herein may promote intrinsic hyaluronic acid (HA) stimulation. Compositions and methods as described herein may promote production of high molecular weight HA (HMW-HA). In some embodiments, the compositions described herein promote HA synthesis. In some embodiments, the compositions described herein described herein promote gene expression of genes involved in HA synthesis (e.g., HAS2, HYAL2, EGR3).

Hyaluronic Acid

Described herein are compositions comprising hyaluronic acid. In some embodiments, the hyaluronic acid is high molecular weight hyaluronic acid. In some embodiments, the hyaluronic acid is synthetic. In some embodiments, the hyaluronic acid comprises improved water binding capacity. In some embodiments, the hyaluronic acid is cross-linked.

Generally, the term "hyaluronic acid" can also encompass all variants and combinations of variants of hyaluronic acid, hyaluronate or hyaluronan, of various chain lengths and charge states, as well as with various chemical modifications, including crosslinking. In some instances, hyaluronic acid comprises hyaluronate salts of hyaluronic acid with various counter ions, such as sodium hyaluronate. Various modifications of the hyaluronic acid are also encompassed by the term, such as oxidation, e.g. oxidation of —CH2OH groups to —CHO and/or —COOH; periodate oxidation of vicinal hydroxyl groups, optionally followed by reduction, e.g. reduction of —CHO to —CH2OH or coupling with amines to form imines followed by reduction to secondary amines; sulphation; deamidation, optionally followed by deamination or amide formation with new acids; esterification; crosslinking; substitutions with various compounds, e.g. using a crosslinking agent or a carbodiimide assisted coupling; including coupling of different molecules, such as proteins, peptides and active drug components, to hyaluronic acid; and deacetylation. Other examples of modifications are isourea, hydrazide, bromocyan, monoepoxide and monosulfone couplings.

Compositions as described herein, in some embodiments, comprise sodium hyaluronate crosspolymer. Sodium hyaluronate crosspolymer is a high molecular weight synthetic hyaluronic acid derived from a non-animal source with high water-binding capacity and moisturizing abilities. Sodium hyaluronate crosspolymer is also a scavenger of damaging free radicals and has a unique gel structure with gel domains that hold tightly bound water.

In some embodiments, the sodium hyaluronate crosspolymer is provided at least or about 0.0001%, 0.0005%, 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4.0% by weight (wt. %). In some embodiments, the sodium hyaluronate crosspolymer is provided at about 0.5% by weight. In some embodiments, the sodium hyaluronate crosspolymer is provided in a range of about 0.0001% to about 4.0%, about 0.001% to about 4.0%, about 0.01% to about 3.0%, about 0.1% to about 2.5%, or about 0.50% to about 1.5% by weight.

Peptides

Peptides as described herein, in some embodiments, promote intrinsic hyaluronic acid (HA) stimulation. In some embodiments, the peptides described herein promote HA synthesis. In some embodiments, the peptides (e.g., octapeptide) described herein promote production of high molecular weight HA (HMW-HA). In some embodiments, the peptides described herein promote gene expression of genes involved in HA synthesis (e.g., HAS2, HYAL2, EGR3).

Compositions as described herein comprise a varying concentration of peptide. In some instances, a peptide is present at about 50 ppm or less to 1000, 5000, 10000, 50000, 100000, 500000 ppm or more, e.g., 100 ppm of the peptide. In some instances, a peptide is present at about 1, 2, 3, 4, 5, 6, 7, 8, 9, 10, 15, 20, 25, 50, 75, 100, 200, 300, 400, 500, 600, 700, 800, 900, 1000, or more than 1000 ppm. In some instances, a peptide is present in a range of about 1 to about 100, about 1 to about 50, about 1 to about 40, about 1 to about 30, about 1 to about 20, about 1 to about 10, about 5 to about 90, about 10 to about 80, about 20 to about 60, or about 30 to about 50 ppm. In some instances, a peptide is present at about 1, 2, 3, 4, 5, 6, 7, 8, 9, 10, 15, 20, 25, 50, 75, 100, 200, 300, 400, 500, 600, 700, 800, 900, 1000, or more than 1000 microgram per milliliter (ug/mL). In some instances, a peptide is present in a range of about 1 to about 100, about 1 to about 50, about 1 to about 40, about 1 to about 30, about 1 to about 20, about 1 to about 10, about 5 to about 90, about 10 to about 80, about 20 to about 60, or about 30 to about 50 microgram per milliliter. In some instances, a peptide is present from about 0.01% to about 10%, about 0.01% to about 0.02%, about 0.01% to about 0.03%, about 0.01% to about 0.04%, about 0.01% to about 0.05%, about 0.01% to about 0.1%, about 1% to about 5%, or about 1% to about 10% by weight (wt. %).

Compositions as described herein, in some embodiments, comprise a plurality of peptides. In some instances, a peptide of the plurality of peptides is present at about 50 ppm or less to 1000, 5000, 10000, 50000, 100000, 500000 ppm or more, e.g., 100 ppm of the peptide, or any other suitable amount. In some instances, a peptide of the plurality of peptides is present at about 1, 2, 3, 4, 5, 6, 7, 8, 9, 10, 15, 20, 25, 50, 75, 100, 200, 300, 400, 500, 600, 700, 800, 900, 1000, or more than 1000 ppm. In some instances, a peptide of the plurality of peptides is present in a range of about 1 to about 100, about 1 to about 50, about 1 to about 40, about 1 to about 30, about 1 to about 20, about 1 to about 10, about 5 to about 90, about 10 to about 80, about 20 to about 60, or about 30 to about 50 ppm. In some instances, a peptide of the plurality of peptides is present at about 1, 2, 3, 4, 5, 6, 7, 8, 9, 10, 15, 20, 25, 50, 75, 100, 200, 300, 400, 500, 600, 700, 800, 900, 1000, or more than 1000 microgram per milliliter (ug/mL). In some instances, a peptide of the plurality of peptides is present in a range of about 1 to about 100, about 1 to about 50, about 1 to about 40, about 1 to about 30, about 1 to about 20, about 1 to about 10, about 5 to about 90, about 10 to about 80, about 20 to about 60, or about 30 to about 50 microgram per milliliter. In some instances, a peptide of the plurality of peptides is present from about 0.01% to about 10%, about 0.01% to about 0.02%, about 0.01% to about 0.03%, about 0.01% to about 0.04%, about 0.01% to about 0.05%, about 0.01% to about 0.1%, about 1% to about 5%, or about 1% to about 10% by weight (wt. %). In some embodiments, a peptide of the plurality of peptides is provided at least or about 0.00001%, 0.0003%, 0.0005%, 0.001%, 0.001%, 0.005%, 0.0055%, 0.01%, 0.02%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, a peptide of the plurality of peptides is provided in a range of about 0.25% to about 10%, about 0.5% to about 8%, about 0.75% to about 6%, or about 1% to about 4% by weight. In some embodiments, each peptide of the plurality of peptides is provided in a range of about 0.001% to about 6%, about 0.002% to about 4%, about 0.01% to about 3%, or about 0.02% to about 2% by weight.

In some embodiments, compositions described herein comprise hexapeptide-11, an octapeptide, a synthetic peptide, or combinations thereof. In some embodiments, the synthetic peptide is tetradecyl-diaminobutyroylvalyl-diaminobutyric urea trifluoroacetate.

In some embodiments, the hexapeptide-11 is provided at least or about 0.00001%, 0.0003%, 0.0005%, 0.001%, 0.001%, 0.005%, 0.0055%, 0.01%, 0.02%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, 20%, 30%, 40%, 50%, 60%, 70%, 80%, 90% or more than 90% by weight (wt. %). In some embodiments, the hexapeptide-11 is provided in a range of about 0.25% to about 10%, about 0.5% to about 8%, about 0.75% to about 6%, or about 1% to about 4% by weight. In some embodiments, the hexapeptide-11 is provided in a range of about 0.001% to about 6%, about 0.002% to about 4%, about 0.01% to about 3%, or about 0.02% to about 2%. In some embodiments, the hexapeptide-11 is provided in a range of about 0.005% to about 0.02% by weight. In some embodiments, the hexapeptide-11 is provided at least or about 5, 10, 20, 25, 50, 75, 100, 150, 200, 250, or more than 250 ppm. In some embodiments, the hexapeptide-11 is provided in a range of about 25 to about 250, about 50 to about 200, or about 75 to about 150 ppm. In some embodiments, the hexapeptide-11 is provided in a range of about 10 to about 100 ppm. In some embodiments, the hexapeptide-11 is provided at least or about 5, 10, 20, 25, 50, 75, 100, 150, 200, 250, or more than 250 microgram per milliliter (ug/mL). In some embodiments, the hexapeptide-11 is provided in a range of about 25 to about 250, about 50 to about 200, or about 75 to about 150 microgram per milliliter.

In some embodiments, the octapeptide is provided at least or about 0.00001%, 0.0003%, 0.0005%, 0.001%, 0.001%, 0.005%, 0.0055%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the octapeptide is provided in a range of about 0.25% to about 10%, about 0.5% to about 8%, about 0.75% to about 6%, or about 1% to about 4% by weight. In some embodiments, the octapeptide is provided at least or about 0.25, 0.5, 0.75, 1, 1.5, 2, 2.5, 3, 3.5, 4, 5, 6, 7, 8, 9, 10, 15, 20, 25, or more than 25 ppm. In some embodiments, the octapeptide is provided in a range of about 1 to about 10 ppm. In some embodiments, the octapeptide is provided in a range of about 0.25 to about 10, about 0.5 to about 8, about 1 to about 6, or about 2 to about 4 ppm. In some embodiments, the octapeptide is provided at least or about 0.25, 0.5, 0.75, 1, 1.5, 2, 2.5, 3, 3.5, 4, 5, 6, 7, 8, 9, 10, 15, 20, 25, or more than 25 microgram per milliliter (ug/mL). In some embodiments, the octapeptide is provided at least or about 25, 30, 35, 40, 45, 50, 55, 60, 65, 70, 75, 80, 85, 90, 95, 100, 110, 120, 130, 140, 150, 160, 170, 180, 190, 200 or more than 200 microgram per milliliter (ug/mL). In some embodiments, the octapeptide is provided in a range of about 0.25 to about 10, about 0.5 to about 8, about 1 to about 6, or about 2 to about 4 microgram per milliliter. In some embodiments, the octapeptide is provided in a range of about 25 to about 200, about 25 to about 150, about 50 to about 150, about 50 to about 125, about 10 to about 60, or about 20 to about 40 microgram per milliliter.

In some embodiments, the synthetic peptide is provided at least or about 0.00001%, 0.0003%, 0.0005%, 0.001%, 0.001%, 0.005%, 0.0055%, 0.01%, 0.02%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, 20%, 30%, 40%, 50%, 60%, 70%, 80%, 90% or more than 90% by weight (wt. %). In some embodiments, the synthetic peptide is provided in a range of about 0.25% to about 10%, about 0.5% to about 8%, about 0.75% to about 6%, or about 1% to about 4% by weight. In some embodiments, the synthetic peptide is provided in a range of about 0.001% to about 6%, about 0.002% to about 4%, about 0.01% to about 3%, or about 0.02% to about 2%. In some embodiments, the synthetic peptide is provided in a range of about 0.005% to about 0.02% by weight. In some embodiments, the synthetic peptide is provided at least or about 0.25, 0.5, 0.75, 1, 1.5, 2, 2.5, 3, 3.5, 4, 5, 10, 20, 25, 50, 75, 100, 150, 200, 250, or more than 250 ppm. In some embodiments, the synthetic peptide is provided in a range of about 25 to about 250, about 50 to about 200, or about 75 to about 150 ppm. In some embodiments, the synthetic peptide is provided at least or about 5, 10, 20, 25, 50, 75, 100, 150, 200, 250, or more than 250 microgram per milliliter (ug/mL). In some embodiments, the synthetic peptide is provided at least or about 5250, 300, 350, 400, 450, 500, 550, 600, 650, 700, 750, 800, 850, 900, 950, 1000 or more than 1000 microgram per milliliter (ug/mL). In some embodiments, the synthetic peptide is provided in a range of about 5 to about 1000, about 10 to about 900, about 30 to about 800, about 50 to about 700, about 60 to about 600, about 100 to about 800, or about 100 to about 500 microgram per milliliter (ug/mL). In some embodiments, the synthetic peptide is provided in a range of about 25 to about 250, about 50 to about 200, or about 75 to about 150 microgram per milliliter (ug/mL). In some embodiments, the synthetic peptide is a synthetic tripeptide. In some embodiments, the synthetic peptide is tetradecyl-diaminobutyroylvalyl-diaminobutyric urea trifluoroacetate.

In some embodiments, the tripeptide-1 is provided at least or about 0.00001%, 0.0003%, 0.0005%, 0.001%, 0.001%, 0.005%, 0.0055%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the tripeptide-1 is provided in a range of about 0.25% to about 10%, about 0.5% to about 8%, about 0.75% to about 6%, or about 1% to about 4% by weight. In some embodiments, the tripeptide-1 is provided at least or about 0.25, 0.5, 0.75, 1, 1.5, 2, 2.5, 3, 3.5, 4, 5, 6, 7, 8, 9, 10, 15, 20, 25, or more than 25 ppm. In some embodiments, the tripeptide-1 is provided in a range of about 0.25 to about 10, about 0.5 to about 8, about 1 to about 6, or about 2 to about 4 ppm. In some embodiments, the tripeptide-1 is provided in a range of about 1 to about 10 ppm. In some embodiments, the tripeptide-1 is provided at least or about 0.25, 0.5, 0.75, 1, 1.5, 2, 2.5, 3, 3.5, 4, 5, 6, 7, 8, 9, 10, 15, 20, 25, or more than 25 microgram per milliliter (ug/mL). In some embodiments, the tripeptide-1 is provided in a range of about 0.25 to about 10, about 0.5 to about 8, about 1 to about 6, or about 2 to about 4 microgram per milliliter.

In some embodiments, the hexapeptide-12 is provided at least or about 0.00001%, 0.0003%, 0.0005%, 0.001%, 0.001%, 0.005%, 0.0055%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the hexapeptide-12 is provided in a range of about 0.25% to about 10%, about 0.5% to about 8%, about 0.75% to about 6%, or about 1% to about 4% by weight. In some embodiments, the hexapeptide-12 is provided at least or about 0.25, 0.5, 0.75, 1, 1.5, 2, 2.5, 3, 3.5, 4, 5, 6, 7, 8, 9, 10, 15, 20, 25, or more than 25 ppm. In some embodiments, the hexapeptide-12 is provided in a range of about 1 to about 10 ppm. In some embodiments, the hexapeptide-12 is provided in a range of about 0.25 to about 10, about 0.5 to about 8, about 1 to about 6, or about 2 to about 4 ppm. In some embodiments, the hexapeptide-12 is provided at least or about 0.25, 0.5, 0.75, 1, 1.5, 2, 2.5, 3, 3.5, 4, 5, 6, 7, 8, 9, 10, 15, 20, 25, or more than 25 microgram per milliliter (ug/mL). In some embodiments, the hexapeptide-12 is provided in a range of about 0.25 to about 10, about 0.5 to about 8, about 1 to about 6, or about 2 to about 4 microgram per milliliter.

In example embodiments, a weight ratio for the first peptide to the second peptide in a topical composition is 1 part first peptide to 0.2 to 10 parts second peptide, 1 to 10 parts second peptide, 1 to 8 parts second peptide, or 1 to 5.5 parts second peptide. The following nomenclature is employed herein to refer to various amino acids: Alanine (also referred to herein as "Ala" or "A"), Arginine (also referred to herein as "Arg" or "R"), Asparagine (also referred to herein as "Asn" or "N"), Aspartic acid (also referred to herein as "Asp" or "D"), Cysteine (also referred to herein as "Cys" or "C"), Glutamic acid (also referred to herein as "Glu" or "E"), Glutamine (also referred to herein as "Gln" or "Q"), Glycine (also referred to herein as "Gly" or "G"), Histidine (also referred to herein as "His" or "H"), Isoleucine (also referred to herein as "Ile" or "I"), Leucine (also referred to herein as "Leu" or "L"), Lysine (also referred to herein as "Lys" or "K"), Methionine (also referred to herein as "Met" or "M"), Phenylalanine (also referred to herein as "Phe" or "F"), Proline (also referred to herein as "Pro" or "P"), Serine (also referred to herein as "Ser" or "S"), Threonine (also referred to herein as "Thr" or "T"), Tryptophan (also referred to herein as "Trp" or "W"), Tyrosine (also referred to herein as "Tyr" or "Y"), Valine (also referred to herein as "Val" or "V").

In some embodiments, the first peptide is a dipeptide. Suitable dipeptides include but are not limited to those having the following sequence of amino acids: KK, KP, CK, KC, KT, DF, NF, VW, YR, or TT. In some embodiments, the dipeptide has the following amino acid sequence: KV. In other embodiments, the first peptide is a tripeptide. Suitable tripeptides include but are not limited to those having the following sequence of amino acids: HGG, RKR, GHK, GKH, GGH, GHG, KFK, or KPK. In some embodiments, the tripeptide has the following amino acid sequence: KVK. In some embodiments, the first peptide is a tetrapeptide. Suitable tetrapeptides include but are not limited to those having the following sequence of amino acids: GQPR (SEQ ID NO: 9), KTFK (SEQ ID NO: 10), AQTR (SEQ ID NO: 11), or RSRK (SEQ ID NO: 12). In some embodiments, the tetrapeptide has the following sequence of amino acids: KDVY (SEQ ID NO: 13). In some embodiments, the second peptide is a pentapeptide. Suitable pentapeptides include but are not limited to those having the following sequence of amino acids: KTTKS (SEQ ID NO: 14), YGGFX (SEQ ID NO: 15), or KLAAK (SEQ ID NO: 16). In some embodiments, the second peptide is a hexapeptide. Suitable hexapeptides include but are not limited to those having the following sequence of amino acids: VGVAPG (SEQ ID NO: 17) or GKTTKS (SEQ ID NO: 18). In some embodiments, the hexapeptide has the following sequence of amino acids: FVAPFP (SEQ ID NO: 19). In some embodiments, the second peptide is a heptapeptide. Suitable heptapeptides include but are not limited to one having an amino acid sequence RGYYLLE (SEQ ID NO: 20), or Heptapeptide-6 (a pro-sirtuin peptide). The compositions may include two or more peptides, e.g., two dipeptides and one pentapeptide; one tripeptide and one hexapeptide; one dipeptide, one tripeptide, and one heptapeptide, or the like, provided that the composition contains at least one dipeptide, tripeptide, or tetrapeptide and at least one pentapeptide, hexapeptide, or heptapeptide. In some embodiments, compositions described herein comprise a hexapeptide, an octapeptide, a synthetic peptide, or combinations thereof. In some embodiments, the one or more hexapeptide is hexapeptide-11. In some embodiments, the one or more peptides is tetradecyl-diaminobutyroylvalyldiaminobutyric urea trifluoroacetate.

The peptide can be functionalized. For example, the peptide can be functionalized with a fatty acid, e.g., myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, palmitic acid, stearic acid, arachidic acid, behenic acid, lignoceric acid, cerotic acid, or the like. Examples include palmitoyl hexapeptide-12 (Pal-VGVAPG (SEQ ID NO: 21)), palmitoyl tripeptide-1 (Pal-GHK), myristoyl hexapeptide-12 (Myr-VGVAPG (SEQ ID NO: 22)), and myristoyl tripeptide-1 (Myr-GHK). Palmitoyl or myristoyl functionalization can be desirable in certain embodiments as it exhibits enhanced penetration when compared to other fatty acids. In some embodiments, the peptide is functionalized with a chemical group. For example, the peptide is functionalized with acetyl. Examples include acetyl hexapeptide-38 and acetyl tetrapeptide-2. In some instances, the peptide is functionalized with a functional group comprising no more than 14 carbons. In some instances, the peptide is functionalized with a functional group comprising no more than 3, 4, 5, 6, 7, 8, 9, 10, 11, 12, 13, 14, 15, 16, 17, 18, 19, 20, or more than 20 carbons. In some instances, the peptide is non-palmitoylated. Without wishing to be limited to a particular theory, incorporation of the peptide in a liposome, in some embodiments, increases the lipophilicity of a peptide that is functionalized or is not functionalized.

Some embodiments of the methods and compositions provided herein include as a first peptide glycine-histidine-lysine (GHK). GHK is a peptide sequence that is rarely found in the class of proteins in general, but is frequently found in extracellular matrix proteins. The small size of GHK permits it to approach membrane receptors far more easily than larger peptides. Further, its unique, copper-binding structure enhances copper transport into and out of cells and promotes wound healing through several different but related pathways. Due to its strong copper binding structure, GHK can be provided in the form of GHK-Cu (copper-bound GHK form).

In some embodiments, compositions described herein comprise an octapeptide. In some embodiments, the octapeptide comprises an amino acid sequence GDGDGASA (SEQ ID NO: 1), GPMGPSGP (SEQ ID NO: 2), GLGPGARA (SEQ ID NO: 3), GPQGFQGP (SEQ ID NO: 4), GPHGVREA (SEQ ID NO: 5), GPMGPRGP (SEQ ID NO: 6), GPGKNGDD (SEQ ID NO: 7), or GPMGPRGP (SEQ ID NO: 8). In some embodiments, the octapeptide comprises an amino acid sequence GDGDGASA (SEQ ID NO: 1). In some embodiments, the octapeptide comprises an amino acid sequence GPMGPSGP (SEQ ID NO: 2). In some embodiments, the octapeptide comprises an amino acid sequence GLGPGARA (SEQ ID NO: 3). In some embodiments, the octapeptide comprises an amino acid sequence GPQGFQGP (SEQ ID NO: 4). In some embodiments, the octapeptide comprises an amino acid sequence GPHGVREA (SEQ ID NO: 5). In some embodiments, the octapeptide comprises an amino acid sequence GPMGPRGP (SEQ ID NO: 6). In some embodiments, the octapeptide comprises an amino acid sequence GPGKNGDD (SEQ ID NO: 7). In some embodiments, the octapeptide comprises an amino acid sequence GPMGPRGP (SEQ ID NO: 8).

The peptides can advantageously be provided in a base for suitable for combining with other components of a liposomal composition. The base can include one or more components such as a thickener/binding agent (e.g., pentaerythrityl tetraisostearate), an emollient/dispersing agent (e.g., caprylic/capric triglyceride), a solvent (e.g., propylene carbonate), and/or a rheology modifier/antisettling agent (e.g., disteardimonium hectorite).

Liposomes

Described herein are liposomal compositions for improved distribution, efficacy, bioavailability, and/or activity. Liposomal compositions may improve distribution, efficacy, bioavailability, and/or activity of the active ingredient by improving delivery and tissue (e.g. skin) penetration. In some instances, improved delivery and skin penetration result from the active ingredient being incorporated (e.g. encapsulated) in a liposome. In some instances, the active ingredient is a peptide that is encapsulated in a liposome.

Liposomal compositions as described herein may comprise a peptide encapsulated in a liposome. In some embodiments, the peptide is hexapeptide-11 In some embodiments, the peptide is functionalized with a palmitoyl group. In some embodiments, the peptide is functionalized with an acetyl group.

Liposomal compositions as described herein may comprise various ingredients encapsulated in a liposome. In some embodiments, the ingredient is lactoferrin. In some embodiments, the ingredient is phosphatidylserine. In some embodiments, the ingredient is *Ledum Palustre* extract. In some embodiments, the ingredient is *Arnica Montana* extract. In some embodiments, the ingredient is sodium hyaluronate. In some embodiments, the ingredient is larger than 50 kDa.

Lecithin and other phospholipids may be used to prepare liposomes containing the peptide compositions as described herein. In some embodiments, liposomes are used to prepare one or more peptides. In some embodiments, the peptide is functionalized with an acetyl group. Formation of lipid vesicles occurs when phospholipids such as lecithin are placed in water and consequently form one bilayer or a series of bilayers, each separated by water molecules, once enough energy is supplied. Liposomes can be created by sonicating phospholipids in water. Low shear rates create multilamellar liposomes. Continued high-shear sonication tends to form smaller unilamellar liposomes. Hydrophobic chemicals can be dissolved into the phospholipid bilayer membrane. The lipid bilayers of the liposomes deliver the peptide compositions as described herein.

The phospholipids used to prepare the liposomal compositions described herein may comprise a transition phase temperature of about 10° C. to about 25° C. In some instances, the phospholipids comprise a transition phase temperature of about 10° C., 12° C., 14° C., 16° C., 18° C., 20° C., 22° C., 24° C., 26° C., 28° C., 30° C., 32° C., 34° C., 36° C., 38° C., 40° C., or more than 40° C. In some instances, the phospholipids comprise a transition phase temperature in a range of about 10° C. to about 40° C., about 12° C. to about 36° C., about 14° C. to about 32° C., about 16° C. to about 20° C., or about 21° C. to about 25° C.

The topical composition may contain micelles, or an aggregate of surfactant molecules dispersed in an aqueous solution. Micelles may be prepared by dispersing an oil solvent in an aqueous solution comprising a surfactant, where the surfactant concentration exceeds the critical micelle concentration. The resulting composition contains micelles, i.e., spherical oil droplets.

The liposomal composition may contain micelles, or an aggregate of surfactant molecules dispersed in an aqueous solution. Micelles may be prepared by dispersing an oil solvent in an aqueous solution comprising a surfactant, where the surfactant concentration exceeds the critical micelle concentration. The resulting formulation contains micelles, i.e., spherical oil droplets surrounded by a membrane of polar surfactant molecules, dispersed in the aqueous solvent.

Described herein, in some embodiments, are methods for preparing a composition comprising a peptide encapsulated in a liposome, comprising: combining the peptide and a solvent to form a mixture; and contacting the mixture with an aqueous solution comprising liposomes. In some instances, the contacting occurs at a temperature between about 10° C. and about 25° C. In some instances, the contacting occurs at a temperature of about 10° C., 12° C., 14° C., 16° C., 18° C., 20° C., 22° C., 24° C., 26° C., 28° C., 30° C., 32° C., 34° C., 36° C., 38° C., 40° C., or more than 40° C. In some instances, the contacting occurs at a temperature in a range of about 10° C. to about 40° C., about 12° C. to about 36° C., about 14° C. to about 32° C., about 16° C. to about 20° C., or about 21° C. to about 25° C.

Methods for preparing a composition comprising a peptide encapsulated in a liposome may comprise use of a solvent. In some instances, the solvent is water. In some instances, the solvent is an organic solvent. Exemplary organic solvents include, but are not limited to, petroleum ether, cyclohexane, toluene, carbon tetrachloride, dichloromethane, chloroform, diethyl ether, diisopropyl ether, ethyl acetate, butanol, n-propanol, ethanol, methanol, polyethylene glycol, propylene glycol, and pyridine. In some instances, the solvent is a glycol. In some instances, the solvent is butylene glycol. In some instances, the solvent is caprylyl glycol. In some instances, the solvent is propanediol (propylene glycol).

The solvent may be used at various percentages. In some instances, the solvent is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10%. The solvent may be propanediol, butylene glycol, or caprylyl glycol.

Methods as described herein, in some embodiments, comprises combining the peptide and a solvent to form a mixture; and contacting the mixture with an aqueous solution comprising liposomes, wherein the aqueous solution comprises a percentage of water and a percentage of liposomes. In some instances, the aqueous solution comprises at least or about 20%, 30%, 40%, 50%, 60%, 70%, 80%, 90%, or more than 90% water. In some instances, the aqueous solution comprises water in a range of about 10% to about 95%, about 20% to about 90%, about 30% to about 85%, about 40% to about 80%, or about 50% to about 60%. In some instances, the aqueous solution comprises at least or about 20%, 30%, 40%, 50%, 60%, or more than 60% liposomes. In some instances, the aqueous solution comprises liposomes in a range of about 10% to about 80%, about 20% to about 70%, or about 30% to about 60%. A ratio of liposomes to water may be in a range of about 1:9 to about 3:7. In some instances, the ratio of liposomes to water may be at least or about 1:10, 1:9, 1:8, 1:7, 1:6, 1:5, 1:4, 1:3, or 1:2.

Methods for generation of liposomal compositions as described herein may result in an entrapment efficacy of no more than 100%. In some instances, the entrapment efficacy is no more than 50%, 60%, 70%, 80%, 90%, 95%, 99%, or 99.5%.

Described herein are liposomal compositions, wherein the peptide comprises a percentage of the composition. In some embodiments, the peptide is provided at least or about 0.0001%, 0.0005%, 0.00055%, 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% of the composition. In some embodiments, the peptide is provided at least or about 10%, 11%, 12%, 13%, 14%, 15%, 16%, 17%, 18%, 19%, 20%, 22%, 24%, 26%, 28%, 30% or more than 30% of the composition. In some embodiments, the peptide is provided in a range of about 0.001% to about 6%, about 0.002% to about 4%, about 0.01% to about 5%, or about 0.02% to about 2% by weight. In some embodiments, the peptide is provided at about 0.03% of the composition.

Described herein are liposomal compositions, wherein the liposomes comprise a percentage of the composition. In some embodiments, the liposomes are provided at least or about 10%, 11%, 12%, 13%, 14%, 15%, 16%, 17%, 18%, 19%, 20%, 22%, 24%, 26%, 28%, 30% or more than 30% of the composition. In some embodiments, the liposomes are provided in a range of about 5% to about 90%, about 10% to about 80%, about 20% to about 70%, about 30% to about 60%, about 10% to about 30%, or about 20% to about 40%. In some embodiments, the liposomes are provided at about 30%. In some embodiments, the liposomes are provided at 27%.

Liposomal compositions as described herein, in some embodiments, comprise an average particle size of at most 220 nanometers (nm). In some instances, the average particle size is at most 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 230 nm, 240 nm, 250 nm, 260 nm, 270 nm, 280 nm, 290 nm, 300 nm, 320 nm, 340 nm, 360 nm, 380 nm, or 400 nm. In some instances, the average particle size is about 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 230 nm, 240 nm, 250 nm, 260 nm, 270 nm, 280 nm, 290 nm, 300 nm, 320 nm, 340 nm, 360 nm, 380 nm, or 400 nm. In some instances, the average particle size is in a range of about 50 nm to about 500 nm, about 100 nm to about 400 nm, about 150 nm to about 220 nm, about 180 nm to about 220 nm, or about 190 nm to about 210 nm.

In some instances, the liposomal compositions comprise an active agent that has a molecular weight of no more than about 600 Daltons (Da). In some instances, the active agent has a molecular weight of at least or about 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, or more than 1000 Daltons (Da). In some instances, the active agent has a molecular weight of at least or about 1000, 1100, 1200, 1300, 1400, 1500, 1600, 1700, 1800, 1900, 2000, 2100, 2200, 2300, 2400, 2500, 2600, 2700, 2800, 2900, 3000, 4000, 5000, 6000, or more than 6000 Daltons (Da). In some instances, the active agent has a molecular weight in a range of about 50 to about 1000, about 100 to about 900, about 200 to about 800, about 300 to about 700, or about 400 to about 600 Daltons (Da). In some instances, the active agent is a peptide. In some instances, the active agent is a peptide encapsulated in a liposome.

A polydispersity index (PdI) of a liposomal composition as described herein, in some embodiments, is in a range of 0 to about 0.2. In some instances, the polydispersity index is about 0.01, 0.025, 0.05, 0.1, 0.25, 0.3, 0.35, 0.4, 0.45, 0.5, 0.55, 0.6, 0.65, 0.7, 0.75, or 0.8. In some instances, the polydispersity index is in a range of about 0.01 to about 0.8, about 0.025 to about 0.75, about 0.05 to about 0.6, or about 0.1 to about 0.3.

In some instances, an intercept of a liposomal composition as described herein is in a range of about 0.85 to about 0.95. In some instances, the intercept is the amplitude. In some instances, the intercept is at least or about 0.65, 0.70, 0.75, 0.80, 0.85, 0.90, or 0.95.

In some embodiments, the liposomes comprise propanediol, lecithin, or a combination thereof. In some embodiments, the propanediol is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the propanediol is provided in a range of about 0.001% to about 6%, about 0.002% to about 4%, about 0.01% to about 3%, or about 0.02% to about 2% by weight. In some embodiments, the lecithin is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the lecithin is provided in a range of about 0.001% to about 6%, about 0.002% to about 4%, about 0.01% to about 3%, or about 0.02% to about 2% by weight. In some embodiments, the liposomes comprise propanediol and lecithin. In some embodiments, the propanediol and lecithin are provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the propanediol and lecithin are provided in a range of about 0.001% to about 6%, about 0.002% to about 4%, about 0.01% to about 3%, or about 0.02% to about 2% by weight. In some embodiments, the propanediol and lecithin are provided at about 0.90% by weight Described herein are liposomal compositions comprising improved distribution, efficacy, bioavailability, and/or activity. The liposomal compositions may comprise improved distribution, efficacy, bioavailability, and/or activity as compared to compositions not comprising liposomes. In some instances, the distribution is improved by at least or about 0.5×, 1.0×, 1.5×, 2.0×, 2.5×, 3.0×, 4.0×, 4.5×, 5×, or more than 5× as compared to compositions not comprising liposomes. In some instances, the efficacy is improved by at least or about 0.5×, 1.0×, 1.5×, 2.0×, 2.5×, 3.0×, 4.0×, 4.5×, 5×, or more than 5× as compared to compositions not comprising liposomes. In some instances, the bioavailability is improved by at least or about 0.5×, 1.0×, 1.5×, 2.0×, 2.5×, 3.0×, 4.0×, 4.5×, 5×, or more than 5× as compared to compositions not comprising liposomes. In some instances, the activity is improved by at least or about 0.5×, 1.0×, 1.5×, 2.0×, 2.5×, 3.0×, 4.0×, 4.5×, 5×, or more than 5× as compared to compositions not comprising liposomes. The distribution, efficacy, bioavailability, and/or activity may be improved by at least or about 10%, 15%, 20%, 25%, 30%, 35%, 40%, 45%, 50%, 55%, 60%, 65%, 70%, 75%, 80%, 85%, 90%, or more than 90% as compared to compositions not comprising liposomes.

Liposomal compositions and methods as described herein, in some embodiments, are topical compositions. In some instances, the liposomal compositions are oil free. In some instances, the liposomal compositions are preservative free. In some embodiments, the liposomal formulation is an aqueous formulation. In some embodiments, the liposomal formulation is an anhydrous formulation. In some instances, the liposomal composition comprises a pH in a range of about 5 to about 8. In some instances, the liposomal composition comprises a pH of at least or about 2, 3, 4, 5, 6, 7, 8, 9, or 10.

Methods and compositions as described herein may result in improved follicular penetration. In some instances, the follicular penetration is improved by at least or about 0.5×, 1.0×, 1.5×, 2.0×, 2.5×, 3.0×, 4.0×, 4.5×, 5×, or more than 5×. The follicular penetration may be improved by at least or about 10%, 15%, 20%, 25%, 30%, 35%, 40%, 45%, 50%, 55%, 60%, 65%, 70%, 75%, 80%, 85%, 90%, or more than 90%. In some instances, compositions result in follicular penetration of a depth of at least or about 0.5, 0.75, 1, 1.25, 1.5, 2, 2.5, 3, 3.5, 4, 4.5, 5, 5.5, 6, 7, 8, 9, 10, or more than 10 millimeters.

Phosphatidylserine

Compositions as described herein, in some embodiments, comprise phosphatidylserine. Exposure of phosphatidylserine from the inner cell membrane of red blood cells can induce phagocytosis of red blood cells. See Chang C F, Goods B A, Askenase M H, et al. Erythrocyte efferocytosis modulates macrophages towards recovery after intracerebral hemorrhage. *The Journal of clinical investigation.* 2018; 128(2):607-624.

In some embodiments, phosphatidylserine is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the phosphatidylserine is provided in a range of about 0.25% to about 10%, about 0.5% to about 8%, about 0.75% to about 6%, or about 1% to about 4% by weight. In some embodiments, the phosphatidylserine is provided in a range of about 0.001% to about 6%, about 0.002% to about 4%, about 0.005% to about 0.1%, about 0.01% to about 3%, or about 0.02% to about 2% by weight. In some embodiments, the phosphatidylserine is provided in a range of about 0.005% to about 0.02% by weight. In some embodiments, the phosphatidylserine is provided at about 0.05% by weight. In some embodiments, the phosphatidylserine is provided at about 0.25% by weight. In some embodiments, the phosphatidylserine is provided at about 1% by weight. In some embodiments, the phosphatidylserine is provided at least or about 5, 10, 20, 25, 50, 75, 100, 150, 200, 250, 300, 350, 400, 450, 500, 550, 600, 650, 700, 750, 800, 850, 900, 950, 1000 or more than 1000 microgram per milliliter (ug/mL). In some embodiments, the phosphatidylserine is provided in a range of about 5 to about 1000, about 10 to about 900, about 30 to about 800, about 50 to about 700, about 60 to about 600, about 100 to about 600, or about 100 to about 500 microgram per milliliter (ug/mL).

Lactoferrin

Compositions as described herein, in some embodiments, comprise a transferrin. In some embodiments, the transferrin is a lactoferrin. In some embodiments, lactoferrin is encapsulated in a liposome. Lactoferrin has wound healing attributes, promotes proliferation of fibroblasts and increases HA secretion. See Saito S, Takayama Y, Mizumachi K, Suzuki C. Lactoferrin promotes hyaluronan synthesis in human dermal fibroblasts. *Biotechnology letters.* 2011; 33(1):33-39; Takayama Y. Effects of Lactoferrin on Skin Wound Healing. In: *Lactoferrin and its Role in Wound Healing.* 2012:87-100.

In some embodiments, lactoferrin is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the lactoferrin is provided in a range of about 0.005% to about 0.1%, about 0.25% to about 10%, about 0.5% to about 8%, about 0.75% to about 6%, or about 1% to about 4% by weight. In some embodiments, the lactoferrin is provided in a range of about 0.001% to about 6%, about 0.002% to about 4%, about 0.01% to about 2.5%, or about 0.02% to about 2% by weight. In some embodiments, the lactoferrin is provided at about 0.025%. In some embodiments, the lactoferrin is provided at about 0.05%. In some embodiments, the lactoferrin is provided at about 0.10%. In some embodiments, the lactoferrin is provided at least or about 5, 10, 20, 25, 50, 75, 100, 150, 200, 250, 300, 350, 400, 450, 500, 550, 600, 650, 700, 750, 800, 850, 900, 950, 1000 or more than 1000 microgram per milliliter (ug/mL). In some embodiments, the lactoferrin is provided in a range of about 5 to about 1000, about 10 to about 900, about 30 to about 800, about 50 to about 700, about 60 to about 600, or about 100 to about 500 microgram per milliliter (ug/mL).

Hydroxymethoxyphenyl Decanone

Compositions as described herein, in some embodiments, comprise hydroxymethoxyphenyl decanone. In some embodiments, the hydroxymethoxyphenyl decanone is a potent intrinsic hyaluronic acid booster, antioxidant, anti-irritant, or a combination thereof.

In some embodiments, hydroxymethoxyphenyl decanone is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the hydroxymethoxyphenyl decanone is provided in a range of about 0.25% to about 10%, about 0.1% to about 2.5%, about 0.5% to about 8%, about 0.75% to about 6%, or about 1% to about 4% by weight. In some embodiments, the hydroxymethoxyphenyl decanone is provided in a range of about 0.001% to about 6%, about 0.002% to about 4%, about 0.01% to about 3%, or about 0.02% to about 2% by weight.

Tremella Fuciformis

Compositions as described herein, in some embodiments, comprise Tremella fuciformis extract. In some embodiments, the Tremella fuciformis extract is derived from an edible mushroom. In some embodiments, Tremella fuciformis extract provides moisture and antioxidant properties. In some embodiments, Tremella fuciformis extract provides moisture from a natural containing hyaluronic acid.

In some embodiments, Tremella fuciformis extract is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the Tremella fuciformis extract is provided in a range of about 0.25% to about 10%, about 0.1% to about 2.5%, about 0.5% to about 8%, about 0.75% to about 6%, or about 1% to about 4% by weight. In some embodiments, the Tremella fuciformis extract is provided in a range of about 0.001% to about 6%, about 0.002% to about 4%, about 0.01% to about 3%, or about 0.02% to about 2% by weight. In some embodiments, the Tremella fuciformis extract is provided at least or about 5, 10, 20, 25, 50, 75, 100, 150, 200, 250, 300, 350, 400, 450, 500, 550, 600, 650, 700, 750, 800, 850, 900, 950, 1000 or more than 1000 microgram per milliliter (ug/mL). In some embodiments, Tremella fuciformis extract is provided in a range of about 5 to about 1000, about 10 to about 900, about 30 to about 800, about 50 to about 700, about 60 to about 600, about 100 to about 600, or about 100 to about 500 microgram per milliliter (ug/mL).

Chemically Crosslinked Hyaluronic Acid

Compositions as described herein, in some embodiments, comprise a chemically crosslinked hyaluronic acid (e.g., Hylasome™ sodium hyaluronate crosspolymer). In some embodiments, the chemically crosslinked hyaluronic acid is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the chemically crosslinked hyaluronic acid is provided in a range of about 0.005% to about 0.1%, about 0.25% to about 10%, about 0.5% to about 8%, about 0.75% to about 6%, or about 1% to about 4% by weight. In some embodiments, the chemically crosslinked hyaluronic acid is provided in a range of about 0.001% to about 6%, about 0.002% to about 4%, about 0.01% to about 2.5%, or about 0.02% to about 2% by weight. In some embodiments, the chemically crosslinked hyaluronic acid is provided at about 0.025%. In some embodiments, the chemically crosslinked hyaluronic acid is provided at about 0.05%. In some embodiments, the chemically crosslinked hyaluronic acid is provided at about 0.10%. In some embodiments, the chemically crosslinked hyaluronic acid is provided at least or about 5, 10, 20, 25, 50, 75, 100, 150, 200, 250, 300, 350, 400, 450, 500, 550, 600, 650, 700, 750, 800, 850, 900, 950, 1000 or more than 1000 microgram per milliliter (ug/mL). In some embodiments, the chemically crosslinked hyaluronic acid is provided in a range of about 5 to about 1000, about 10 to about 900, about 30 to about 800, about 50 to about 700, about 60 to about 600, or about 100 to about 500 microgram per milliliter (ug/mL).

Other Components

Compositions as described herein, in some embodiments, comprise SymDecanox™ (topical antioxidant). In some embodiments, the SymDecanox™ (topical antioxidant) is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the SymDecanox™ (topical antioxidant) is provided in a range of about 0.005% to about 0.1%, about 0.25% to about 10%, about 0.5% to about 8%, about 0.75% to about 6%, or about 1% to about 4% by weight. In some embodiments, the SymDecanox™ (topical antioxidant) is provided in a range of about 0.001% to about 6%, about 0.002% to about 4%, about 0.01% to about 2.5%, or about 0.02% to about 2% by weight. In some embodiments, the SymDecanox™ (topical antioxidant) is provided at about 0.025%. In some embodiments, the SymDecanox™ (topical antioxidant) is provided at about 0.05%. In some embodiments, the SymDecanox™ (topical antioxidant) is provided at about 0.10%. In some embodiments, the SymDecanox™ (topical antioxidant) is provided at least or about 5, 10, 20, 25, 50, 75, 100, 150, 200, 250, 300, 350, 400, 450, 500, 550, 600, 650, 700, 750, 800, 850, 900, 950, 1000 or more than 1000 microgram per milliliter (ug/mL). In some embodiments, the SymDecanox™ (topical antioxidant) is provided in a range of about 5 to about 1000, about 10 to about 900, about 30 to about 800, about 50 to about 700, about 60 to about 600, or about 100 to about 500 microgram per milliliter (ug/mL).

Compositions as described herein, in some embodiments, comprise Aquaxyl™ (sugar-derived moisturizing agent). In some embodiments, the Aquaxyl™ (sugar-derived moisturizing agent) is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the Aquaxyl™ (sugar-derived moisturizing agent) is provided in a range of about 0.005% to about 0.1%, about 0.25% to about 10%, about 0.5% to about 8%, about 0.75% to about 6%, or about 1% to about 4% by weight. In some embodiments, the Aquaxyl™ (sugar-derived moisturizing agent) is provided in a range of about 0.001% to about 6%, about 0.002% to about 4%, about 0.01% to about 2.5%, or about 0.02% to about 2% by weight. In some embodiments, the Aquaxyl™ (sugar-derived moisturizing agent) is provided at about 0.025%. In some embodiments, the Aquaxyl™ (sugar-derived moisturizing agent) is provided at about 0.05%. In some embodiments, the Aquaxyl™ (sugar-derived moisturizing agent) is provided at about 0.10%. In some embodiments, the Aquaxyl™ (sugar-derived moisturizing agent) is provided at least or about 5, 10, 20, 25, 50, 75, 100, 150, 200, 250, 300, 350, 400, 450, 500, 550, 600, 650, 700, 750, 800, 850, 900, 950, 1000 or more than 1000 microgram per milliliter (ug/mL). In some embodiments, the Aquaxyl™ (sugar-derived moisturizing agent) is provided in a range of about 5 to about 1000, about 10 to about 900, about 30 to about 800, about 50 to about 700, about 60 to about 600, or about 100 to about 500 microgram per milliliter (ug/mL).

Other components can include anti-inflammatory agents, antioxidants, and solubility enhancers. Exemplary anti-irritation agents include, but are not limited to, panthenyl triacetate and naringenin. Panthenyl triacetate and naringenin are natural plant extracts that reduce redness and water loss through the skin. Typical amounts for anti-irritation agents when employed in compositions are from 1% by weight to 4% by weight (wt. %).

Exemplary antioxidant agents include, but are not limited to, *Dunaliella salina* extract and squalane. *Dunaliella salina* extract includes components such as beta carotenes. It can exhibit an antioxidant effect. Typical amounts for anti-inflammatory agents when employed in compositions are from 0.1% by weight to 2.5% by weight (wt. %). In some embodiments, the *Dunaliella salina* extract is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight. In some embodiments, the *Dunaliella salina* extract is provided in a range of about 0.001% to about 4.0%, about 0.01% to about 3.0%, about 0.1% to about 2.5%, or about 0.50% to about 1.5%. In some embodiments, the squalane is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight. In some embodiments, the squalane is provided in a range of about 0.001% to about 4.0%, about 0.01% to about 3.0%, about 0.1% to about 2.5%, or about 0.50% to about 1.5%. In some embodiments, the *Dunaliella salina* extract and the squalane is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight. In some embodiments, the *Dunaliella salina* and the squalane extract is provided in a range of about 0.001% to about 4.0%, about 0.01% to about 3.0%, about 0.1% to about 2.5%, or about 0.50% to about 1.5%.

In some embodiments, the composition comprises a siloxane polymer. In some embodiments, the siloxane polymer is caprylyl methicone. In some embodiments, caprylyl methicone is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4.0% by weight (wt. %). In some embodiments, the caprylyl methicone is provided at about 0.5% by weight. In some embodiments, the caprylyl methicone is provided in a range of about 0.001% to about 4.0%, about 0.01% to about 3.0%, about 0.1% to about 2.5%, or about 0.50% to about 1.5% by weight. In some embodiments, the caprylyl methicone is provided at about 0.25% by weight. In some embodiments, the caprylyl methicone is provided at about 1% by weight.

Bentonite clays can be employed in conjunction with the peptides to provide impart penetration and adsorption properties to the compositions, and can aid in stabilizing emulsions. Other clays, such as hectorite and magnesium aluminum silicate can also be employed. Bentonite or other clays can be modified to yield an organic modified clay compound. Salts (e.g., quaternary ammonium salts) of fatty acids (e.g., hydrogenated fatty acids) can be reacted with hectorite or other clays. As provided herein, fatty acids are referred to and described using conventional nomenclature as is employed by one of skill in the art. A saturated fatty acid includes no carbon-carbon double bonds. An unsaturated fatty acid includes at least one carbon-carbon double bond. A monounsaturated fatty acid includes only one carbon-carbon double bond. A polyunsaturated fatty acid includes two or more carbon-carbon double bonds. Double bonds in fatty acids are generally cis; however, trans double bonds are also possible. The position of double bonds can be indicated by Δn, where n indicates the lower numbered carbon of each pair of double-bonded carbon atoms. A shorthand notation specifying total #carbons: #double bonds, $\Delta_{double\ bond\ positions}$ can be employed. For example, $20{:}4\Delta_{5,8,11,14}$ refers to a fatty acid having 20 carbon atoms and four double bonds, with the double bonds situated between the 5 and 6 carbon atom, the 8 and 9 carbon atom, the 11 and 12 carbon atom, and the 14 and 15 carbon atom, with carbon atom 1 being the carbon of the carboxylic acid group. Stearate (octadecanoate) is a saturated fatty acid. Oleate (cis-Δ9-octadecenoate) is a monounsaturated fatty acid, linolenate (all-cis-Δ9,12,15-octadecatrienoate) is a polyunsaturated fatty acid. Fatty acids suitable for use can comprise from 5 to 30 carbon atoms, e.g., 5, 6, 7, 8, 9, 10, 11, 12, 13, 14, 15, 16, 17, 18, 19, 20, 21, 22, 23, 24, 25, 26, 27, 28, 29, or 30 carbon atoms. The fatty acid can be fully saturated, or can include as many double bonds as are feasible for the chain length. Fatty acids suitable for functionalizing hectorite or other clays include palmitic acid and stearic acid. Dialkyl quaternary cationic modifiers include dipalmoyldimonium chloride and distearyldimonium chloride. Amidoamine quaternary cationic modifiers include palmitamidopropyltrimonium chloride cetearyl alcohol and palmitamidopropyltrimonium chloride.

In some embodiments, the peptides can be in admixture with a suitable carrier, diluent, or excipient, and can contain auxiliary substances such as wetting or emulsifying agents, pH buffering agents, gelling or viscosity enhancing additives, preservatives, scenting agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for compositions include, without limitation, monoglycerides, diglycerides, sulfatides, lysolecithin, phospholipids, saponin, bile acids, and the like. In some embodiments, compositions described herein comprise, phosphatidylserine, phospholipids, tocopherol, ascorbyl palmitate, or combinations thereof. In some embodiments, phosphatidylserine, phospholipids, tocopherol, ascorbyl palmitate, or combinations thereof is provided at 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the phosphatidylserine, phospholipids, tocopherol, ascorbyl palmitate, or combinations thereof is provided in a range of about 0.25% to about 10%, about 0.5% to about 8%, about 0.75% to about 6%, or about 1% to about 4% by weight. In some embodiments, the phosphatidylserine, phospholipids, tocopherol, ascorbyl palmitate, or combinations thereof is provided in a range of about 0.001% to about 6%, about 0.002% to about 4%, about 0.01% to about 3%, or about 0.02% to about 5% by weight. In some embodiments, the additive is betaine. Betaine, in some embodiments, is provided in a range of about 0.001% to about 6%, about 0.002% to about 4%, about 0.01% to about 3%, or about 0.02% to about 5% by weight. In some embodiments, the compositions as described herein comprise caprylyl glycol. In some embodiments, the caprylyl glycol provided in a range of about 0.001% to about 6%, about 0.002% to about 4%, about 0.01% to about 3%, or about 0.02% to about 5% by weight. In some embodiments, the compositions as described herein comprise caprylhydroxamic acid. In some embodiments, the caprylhydroxamic acid provided in a range of about 0.001% to about 6%, about 0.002% to about 4%, about 0.01% to about 3%, or about 0.02% to about 5% by weight. The presence of such additional components can influence the physical state, solubility, stability, rate of release, rate of clearance, and penetration of active ingredients.

The compositions for topical administration comprise the peptide compositions as described herein and a dermatologically acceptable vehicle. The vehicle may be aqueous or nonaqueous. The dermatologically acceptable vehicle used in the topical composition may be in the form of a lotion, a gel, an ointment, a liquid, a cream, or an emulsion. If the vehicle is an emulsion, the emulsion may have a continuous aqueous phase and a discontinuous nonaqueous or oil phase (oil-in-water emulsion), or a continuous nonaqueous or oil phase and a discontinuous aqueous phase (water-in-oil emulsion). When administered topically in liquid or gel form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain coloring and scenting agents.

In certain embodiments, a silicone elastomer (e.g., dimethicone crosspolymer) is employed to increase delivery and penetration of the peptides into the skin. An alternative to increasing molecular weight (as with silicone gums) or adding filler (as with silicone compounds) is to partially crosslink siloxane polymers and disperse this material in an appropriate silicone carrier fluid. The resulting dimethicone crosspolymers (also known as silicone elastomers in the personal care industry) differ from basic polydimethylsiloxane (PDMS) because of the cross-linking between the linear polymers. These materials can be employed in peptide compositions, and also offer benefits in scar treatment, periwound protection and enzyme delivery. In skin care applications, the aesthetics of silicone elastomers (including those with functional groups) and their ability to absorb various oils (e.g., with a dimethicone/vinyl dimethicone crosspolymer such as Dow Corning® 9506 Elastomer Powder) are two of the elastomer's desirable properties. Silicone elastomers have a skin feel different from any of the silicone fluids, described as "smooth," "velvety," and "powdery." It can be modified by controlling the amount of liquid phase in the formula, and therefore the degree of swelling. Due to their film-forming properties, dimethicone crosspolymers can be used as delivery systems for active ingredients such as the peptides described herein, or other composition components such as oil-soluble vitamins and sunscreens. Sunscreens such as octyl methoxycinnamate can be more efficiently delivered from a composition containing a silicone elastomer, producing a higher sun protection factor (SPF). Silicone elastomer blends can be used to enhance SPF in oil-in-water compositions containing organic sunscreens. For example, in testing conducted regarding SPF, the addition of 4% silicone elastomer blend to a sun care composition containing organic sunscreens increased the SPF from 5.7 to 18. This property of the silicone elastomer allows the effectiveness of sunscreen agents in a composition to be maximized while reducing the amount needed to achieve a desired SPF. As a result, composition costs can be reduced along with 0.025%, 0.05%, 0.75%, 1%, 2%, 3%, 4%, 5%, 6%, 7%, 8%, 9% 10%, 11%, 12%, or more than 12% by weight. In some embodiments, pentylene glycol is provided in a range of about 0.01% to about 10%, about 0.025% to about 5%, or about 0.05% to about 1.25% by weight. Suitable solvents for hydrophobic compositions include mineral oils, vegetable oils, and silicone oils. If desired, the peptide compositions as described herein may be dissolved or dispersed in a hydrophobic oil phase, and the oil phase may then be emulsified in an aqueous phase comprising water, alone or in combination with lower alcohols, glycerin, and/or glycols. In some embodiments, an anhydrous composition is applied as the presence of water can result in stinging upon administration to skin tissues subject to laser treatment, chemical peel, dermabrasion, or the like. Anhydrous compositions may also act to prevent the development of water-based irritant contact dermatitis in damaged or sensitive skin, which may produce rashes and skin irritation that may retard wound healing and improvement in skin quality. Tsai, T. F., Maibach, H. I. How irritant is water? An overview. Contact Dermatitis 41(6) (1999): 311-314 (describing contact dermatitis caused by water as an irritant). However, in certain embodiments it may be acceptable to provide water based compositions, or to permit a limited amount of water to be present. For example, water may be present, but at amounts below the threshold at which a stinging sensation when applied to damaged skin may result. Osmotic shock or osmotic stress is a sudden change in the solute concentration around a cell, causing a rapid change in the movement of water across its cell membrane. Under conditions of high concentrations of either salts, substrates or any solute in the supernatant, water is drawn out of the cells through osmosis. This also inhibits the transport of substrates and cofactors into the cell thus "shocking" the cell. Alternatively, at low concentrations of solutes, water enters the cell in large amounts, causing it to swell and either burst or undergo apoptosis. Certain of the compositions as described herein can be advantageously employed where it is desirable to minimize osmotic shock.

Compositions as described herein may comprise varying amounts of solvent. In some embodiments, the solvent is water. In some embodiments, the solvent is at least or about 10%, 15%, 20%, 25%, 30%, 35%, 40%, 45%, 50%, 55%, 60%, 65%, 70%, 75%, 80%, 85%, 90%, 95%, or more than 95% by weight (wt. %). In some embodiments, the solvent is in a range of about 10% to about 95%, about 20% to about 90%, about 30% to about 85%, about 40% to about 80%, or about 50% to about 75% by weight.

Viscosity of the compositions can be maintained at the selected level using a pharmaceutically acceptable thickening agent. Suitable viscosity enhancers or thickeners which may be used to prepare a viscous gel or cream with an aqueous base include sodium polyacrylate, lactoferrin, sodium hyaluronate crosspolymer, phosphatidylserine, or combinations thereof stimulate intrinsic hyaluronic acid production.

In some embodiments, the compositions as described herein stimulate intrinsic hyaluronic acid production by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, the compositions as described herein stimulate intrinsic hyaluronic acid production by at least or about 0.5×, 1.0×, 1.5×, 2.0×, 2.5×, 3.0×, 3.5×, 4.0×, 5.0×, 6.0×, 7.0×, 8.0×, 9.0×, 10×, or more than 10×.

Compositions as described herein may be used with various skin regimens. In some instances, the topical compositions described herein are administered once per day, twice per day, three times per day or more. In some instances, the topical compositions described herein are administered twice per day. The topical compositions described herein, in some embodiments, are administered daily, every day, every alternate day, five days a week, once a week, every other week, two weeks per month, three weeks per month, once a month, twice a month, three times per month, or more. In some embodiments, the topical compositions described herein are administered twice daily, e.g., morning and evening. In some embodiments, the topical compositions described herein are administered for at least 1 day, 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 12 months, 18 months, 2 years, 3 years, 4 years, 5 years, 10 years, or more. In some embodiments, the topical compositions described herein are administered twice daily for at least or about 1 week, 2 weeks, 3 weeks, 1 month, 2 months, 3 months, 4 months, 5 months, 6 months, or more. In some embodiments, the topical compositions described herein are administered once daily, twice daily, three times daily, four times daily, or more than four times daily for at least or about 1 week, 2 weeks, 3 weeks, 1 month, 2 months, 3 months, 4 months, 5 months, 6 months, or more.

Stability Testing

Stability testing of the compositions can be conducted as follows.

High temperature testing is now commonly used as a predictor of long-term stability. High temperature testing can be conducted at 37° C. (98° F.) and 45° C. (113° F.). If a product is stored at 45° C. for three months (and exhibits acceptable stability) then it should be stable at room temperature for two years. A good control temperature is 4° C. (39° F.) where most products will exhibit excellent stability. Sometime, the product is also be subjected to −10° C. (14° F.) for three months.

In some instances, stability of the product is assessed by passing three cycles of temperature testing from −10° C. (14° F.) to 25° C. (77° F.). In such cases, the product is placed at −10° C. for 24 hours and then placed at room temperature (25° C.) for 24 hours. This completes one cycle. An even more rigorous test is a −10° C. to 45° C. five-cycle test. This puts emulsions under a tremendous stress.

The dispersed phase (of an oil-in-water emulsion) has a tendency to separate and rise to the top of the emulsion forming a layer of oil droplets. This phenomenon is called creaming. Creaming is one of the first signs of impending emulsion instability. A test method to predict creaming is centrifugation. Heat the emulsion to 50° C. (122° F.) and centrifuge it for thirty minutes at 3000 rpm. Then inspect the resultant product for signs of creaming.

Both formulas and packaging can be sensitive to the UV radiation. The product is placed in glass and the actual package in a light box that has a broad-spectrum output. Another glass jar completely covered with aluminum foil serves as a control. Discoloration of the product may be observed.

For all the above mentioned tests the color, odor/fragrance, viscosity, pH value, and, if available, particle size uniformity and/or particle agglomeration under the microscope can be observed.

Kits for Non-Invasive Use and Use with Invasive Procedures

Some embodiments of the methods and compositions provided herein include kits comprising peptides and agents that stimulate hyaluronic acid. In some embodiments, kits can be provided to an administering physician, other health care professional, a patient, or a caregiver. In some embodiments, a kit comprises a container which contains the compositions in a suitable topical composition, and instructions for administering the composition to a subject. The kit can optionally also contain one or more additional therapeutic or other agents. For example, a kit containing a peptide composition in topical form can be provided along with other skin care agents, such as, cleansers, occlusive moisturizers, penetrating moisturizers, sunscreens, sunblocks, and the like. The kit may contain the peptide composition in bulk form, or can contain separate doses of the peptide composition for serial or sequential administration. The kit can optionally contain one or more diagnostic tools, administration tools, and/or instructions for use. The kit can contain suitable delivery devices, such as, syringes, pump dispensers, single dose packets, and the like, along with instructions for administering the peptide compositions and any other therapeutic or beneficial agents. The kit can optionally contain instructions for storage, embodiments 1-3, wherein the octapeptide comprises an amino acid sequence GDGDGASA (SEQ ID NO: 1), GPMGPSGP (SEQ ID NO: 2), GLGPGARA (SEQ ID NO: 3), GPQGFQGP (SEQ ID NO: 4), GPHGVREA (SEQ ID NO: 5), GPMGPRGP (SEQ ID NO: 6), GPGKNGDD (SEQ ID NO: 7), or GPMGPRGP (SEQ ID NO: 8). Numbered embodiment 5 comprises the topical composition of numbered embodiments 1-4, wherein the octapeptide comprises an amino acid sequence GDGDGASA (SEQ ID NO: 1). Numbered embodiment 6 comprises the topical composition of numbered embodiments 1-5, wherein the octapeptide comprises an amino acid sequence GPMGPSGP (SEQ ID NO: 2). Numbered embodiment 7 comprises the topical composition of numbered embodiments 1-6, wherein the octapeptide comprises an amino acid sequence GLGPGARA (SEQ ID NO: 3). Numbered embodiment 8 comprises the topical composition of numbered embodiments 1-7, wherein the octapeptide comprises an amino acid sequence GPQGFQGP (SEQ ID NO: 4). Numbered embodiment 9 comprises the topical composition of numbered embodiments 1-8, wherein the octapeptide comprises an amino acid sequence GPHGVREA (SEQ ID NO: 5). Numbered embodiment 10 comprises the topical composition of numbered embodiments 1-9, wherein the octapeptide comprises an amino acid sequence GPMGPRGP (SEQ ID NO: 6). Numbered embodiment 11 comprises the topical composition of numbered embodiments 1-10, wherein the octapeptide comprises an amino acid sequence GPGKNGDD (SEQ ID NO: 7). Numbered embodiment 12 comprises the topical composition of numbered embodiments 1-11, wherein the octapeptide comprises an amino acid sequence GPMGPRGP (SEQ ID NO: 8). Numbered embodiment 13 comprises the topical composition of numbered embodiments 1-12, wherein the hexapeptide is hexapeptide-11. Numbered embodiment 14 comprises the topical composition of numbered embodiments 1-13, wherein the hexapeptide-11 is encapsulated in a liposome. Numbered embodiment 15 comprises the topical composition of numbered embodiments 1-14, further comprising lactoferrin. Numbered embodiment 16 comprises the topical composition of numbered embodiments 1-15, wherein the lactoferrin is encapsulated in a liposome. Numbered embodiment 17 comprises the topical composition of numbered embodiments 1-16, further comprising phosphatidylserine. Numbered embodiment 18 comprises the topical composition of numbered embodiments 1-17, wherein the topical composition further comprises Tremella fuciformis extract. Numbered embodiment 19 comprises the topical composition of numbered embodiments 1-18, wherein the topical composition further comprises sodium hyaluronate crosspolymer. Numbered embodiment 20 comprises the topical composition of numbered embodiments 1-19, wherein the topical composition further comprises hydroxymethoxyphenyl decanone. Numbered embodiment 21 comprises the topical composition of numbered embodiments 1-20, wherein the topical composition is aqueous. Numbered embodiment 22 comprises the topical composition of numbered embodiments 1-21, wherein the octapeptide comprises an amino acid sequence GPMGPSGP (SEQ ID NO: 2) and the hexapeptide is hexapeptide-11. Numbered embodiment 23 comprises the topical composition of numbered embodiments 1-22, further comprising lactoferrin, phosphatidylserine, Tremella fuciformis extract, sodium hyaluronate crosspolymer, hydroxymethoxyphenyl decanone, or combinations thereof. Numbered embodiment 24 comprises the topical composition of numbered embodiments 1-23, wherein the octapeptide comprises an amino acid sequence GLGPGARA (SEQ ID NO: 3) and the hexapeptide is hexapeptide-11. Numbered embodiment 25 comprises the topical composition of numbered embodiments 1-24, further comprising lactoferrin, phosphatidylserine, Tremella fuciformis extract, sodium hyaluronate crosspolymer, hydroxymethoxyphenyl decanone, or combinations thereof. Numbered embodiment 26 comprises the topical composition of numbered embodiments 1-25, wherein the octapeptide comprises an amino acid sequence GPQGFQGP (SEQ ID NO: 4) and the hexapeptide is hexapeptide-11. Numbered embodiment 27 comprises the topical composition of numbered embodiments 1-26, further comprising lactoferrin, phosphatidylserine, Tremella fuciformis extract, sodium hyaluronate crosspolymer, hydroxymethoxyphenyl decanone, or combinations thereof. Numbered embodiment 28 comprises the topical composition of numbered embodiments 1-27, wherein the octapeptide comprises an amino acid sequence GPHGVREA (SEQ ID NO: 5) and the hexapeptide is hexapeptide-11. Numbered embodiment 29 comprises the topical composition of numbered embodiments 1-28, further comprising lactoferrin, phosphatidylserine, Tremella fuciformis extract, sodium hyaluronate crosspolymer, hydroxymethoxyphenyl decanone, or combinations thereof. Numbered embodiment 30 comprises the topical composition of numbered embodiments 1-29, wherein the octapeptide comprises an amino acid sequence GPMGPRGP (SEQ ID NO: 6) and the hexapeptide is hexapeptide-11. Numbered embodiment 31 comprises the topical composition of numbered embodiments 1-30, further comprising lactoferrin, phosphatidylserine, Tremella fuciformis extract, sodium hyaluronate crosspolymer, hydroxymethoxyphenyl decanone, or combinations thereof. Numbered embodiment 32 comprises the topical composition of numbered embodiments 1-31, wherein the octapeptide comprises an amino acid sequence GPGKNGDD (SEQ ID NO: 7) and the hexapeptide is hexapeptide-11. Numbered embodiment 33 comprises the topical composition of numbered embodiments 1-32, further comprising lactoferrin, phosphatidylserine, Tremella fuciformis extract, sodium hyaluronate crosspolymer, hydroxymethoxyphenyl decanone, or combinations thereof. Numbered embodiment 34 comprises the topical composition of numbered embodiments 1-33, wherein the octapeptide comprises an amino acid sequence GPMGPRGP (SEQ ID NO: 8) and the hexapeptide is hexapeptide-11. Numbered embodiment 35 comprises the topical composition of numbered embodiments 1-34, further comprising lactoferrin, phosphatidylserine, Tremella fuciformis extract, sodium hyaluronate crosspolymer, hydroxymethoxyphenyl decanone, or combinations thereof. Numbered embodiment 36 comprises a method for stimulating hyaluronic acid production, comprising administering a topical composition comprising: a synthetic tripeptide; an octapeptide; and a hexapeptide. Numbered embodiment 37 comprises a method of any one of numbered embodiments 1-36, wherein the synthetic tripeptide comprises tetradecyl-diaminobutyroylvalyldiaminobutyric urea trifluoroacetate. Numbered embodiment 38 comprises a method of any one of numbered embodiments 1-37, wherein the octapeptide is encapsulated in a liposome. Numbered embodiment 39 comprises a method of any one of numbered embodiments 1-38, wherein the octapeptide comprises an amino acid sequence GDGDGASA (SEQ ID NO: 1), GPMGPSGP (SEQ ID NO: 2), GLGPGARA (SEQ ID NO: 3), GPQGFQGP (SEQ ID NO: 4), GPHGVREA (SEQ ID NO: 5), GPMGPRGP (SEQ ID NO: 6), GPGKNGDD (SEQ ID NO: 7), or GPMGPRGP (SEQ ID NO: 8). Numbered embodiment 40 comprises a method of any one of numbered embodiments 1-39, wherein the octapeptide comprises an amino acid sequence GDGDGASA (SEQ ID NO: 1). Numbered embodiment 41 comprises a method of any one of numbered embodiments 1-40, wherein the octapeptide comprises an amino acid sequence GPMGPSGP (SEQ ID NO: 2). Numbered embodiment 42 comprises a method of any one of numbered embodiments 1-41, wherein the octapeptide comprises an amino acid sequence GLGPGARA (SEQ ID NO: 3). Numbered embodiment 43 comprises a method of any one of numbered embodiments 1-42, wherein the octapeptide comprises an amino acid sequence GPQGFQGP (SEQ ID NO: 4). Numbered embodiment 44 comprises a method of any one of numbered embodiments 1-43, wherein the octapeptide comprises an amino acid sequence GPHGVREA (SEQ ID NO: 5). Numbered embodiment 45 comprises a method of any one of numbered embodiments 1-44, wherein the octapeptide comprises an amino acid sequence GPMGPRGP (SEQ ID NO: 6). Numbered embodiment 46 comprises a method of any one of numbered embodiments 1-45, wherein the octapeptide comprises an amino acid sequence GPGKNGDD (SEQ ID NO: 7). Numbered embodiment 47 comprises a method of any one of numbered embodiments 1-46, wherein the octapeptide comprises an amino acid sequence GPMGPRGP (SEQ ID NO: 8). Numbered embodiment 48 comprises a method of any one of numbered embodiments 1-47, wherein the hexapeptide is hexapeptide-11. Numbered embodiment 49 comprises a method of any one of numbered embodiments 1-48, wherein the hexapeptide-11 is encapsulated in a liposome. Numbered embodiment 50 comprises a method of any one of numbered embodiments 1-49, wherein the topical composition further comprises lactoferrin. Numbered embodiment 51 comprises a method of any one of numbered embodiments 1-50, wherein the lactoferrin is encapsulated in a liposome. Numbered embodiment 52 comprises a method of any one of numbered embodiments 1-51, wherein the topical composition further comprises phosphatidylserine. Numbered embodiment 53 comprises a method of any one of numbered embodiments 1-52, wherein the topical composition further comprises Tremella fuciformis extract. Numbered embodiment 54 comprises a method of any one of numbered embodiments 1-53, wherein the topical composition further comprises sodium hyaluronate crosspolymer. Numbered embodiment 55 comprises a method of any one of numbered embodiments 1-54, wherein the topical composition further comprises hydroxymethoxyphenyl decanone. Numbered embodiment 56 comprises a method of any one of numbered embodiments 1-55, wherein the octapeptide comprises an amino acid sequence GPMGPSGP (SEQ ID NO: 2) and the hexapeptide is hexapeptide-11. Numbered embodiment 57 comprises a method of any one of numbered embodiments 1-56, wherein the topical composition further comprises lactoferrin, phosphatidylserine, Tremella fuciformis extract, sodium hyaluronate crosspolymer, hydroxymethoxyphenyl decanone, or combinations thereof. Numbered embodiment 58 comprises a method of any one of numbered embodiments 1-57, wherein the octapeptide comprises an amino acid sequence GLGPGARA (SEQ ID NO: 3) and the hexapeptide is hexapeptide-11. Numbered embodiment 59 comprises a method of any one of numbered embodiments 1-58, wherein the topical composition further comprises lactoferrin, phosphatidylserine, Tremella fuciformis extract, sodium hyaluronate crosspolymer, hydroxymethoxyphenyl decanone, or combinations thereof. Numbered embodiment 60 comprises a method of any one of numbered embodiments 1-59, wherein the octapeptide comprises an amino acid sequence GPQGFQGP (SEQ ID NO: 4) and the hexapeptide is hexapeptide-11. Numbered embodiment 61 comprises a method of any one of numbered embodiments 1-60, wherein the topical composition further comprises lactoferrin, phosphatidylserine, Tremella fuciformis extract, sodium hyaluronate crosspolymer, hydroxymethoxyphenyl decanone, or combinations thereof. Numbered embodiment 62 comprises a method of any one of numbered embodiments 1-61, wherein the octapeptide comprises an amino acid sequence GPHGVREA (SEQ ID NO: 5) and the hexapeptide is hexapeptide-11. Numbered embodiment 63 comprises a method of any one of numbered embodiments 1-62, wherein the topical composition further comprises lactoferrin, phosphatidylserine, Tremella fuciformis extract, sodium hyaluronate crosspolymer, hydroxymethoxyphenyl decanone, or combinations thereof. Numbered embodiment 64 comprises a method of any one of numbered embodiments 1-63, wherein the octapeptide comprises an amino acid sequence GPMGPRGP (SEQ ID NO: 6) and the hexapeptide is hexapeptide-11. Numbered embodiment 65 comprises a method of any one of numbered embodiments 1-64, wherein the topical composition further comprises lactoferrin, phosphatidylserine, Tremella fuciformis extract, sodium hyaluronate crosspolymer, hydroxymethoxyphenyl decanone, or combinations thereof. Numbered embodiment 66 comprises a method of any one of numbered embodiments 1-65, wherein the octapeptide comprises an amino acid sequence GPGKNGDD (SEQ ID NO: 7) and the hexapeptide is hexapeptide-11. Numbered embodiment 67 comprises a method of any one of numbered embodiments 1-66, wherein the topical composition further comprises lactoferrin, phosphatidylserine, Tremella fuciformis extract, sodium hyaluronate crosspolymer, hydroxymethoxyphenyl decanone, or combinations thereof. Numbered embodiment 68 comprises a method of any one of numbered embodiments 1-67, wherein the octapeptide comprises an amino acid sequence GPMGPRGP (SEQ ID NO: 8) and the hexapeptide is hexapeptide-11. Numbered embodiment 69 comprises a method of any one of numbered embodiments 1-68, wherein the topical composition further comprises lactoferrin, phosphatidylserine, Tremella fuciformis extract, sodium hyaluronate crosspolymer, hydroxymethoxyphenyl decanone, or combinations thereof. Numbered embodiment 70 comprises a method of any one of numbered embodiments 1-69, wherein the topical composition is aqueous. Numbered embodiment 71 comprises a method of any one of numbered embodiments 1-70, wherein the topical composition improves skin moisture. Numbered embodiment 72 comprises a method of any one of numbered embodiments 1-71, wherein the topical composition reduces appearance of a bruise, an aging spot, or a wrinkle. Numbered embodiment 73 comprises a method of any one of numbered embodiments 1-72, wherein the topical composition is administered 1, 2, 3, 4, 5, 6, 7, or 8 times a day. Numbered embodiment 74 comprises a method of any one of numbered embodiments 1-73, wherein the individual is a human.

EXAMPLES

The following examples are given for the purpose of illustrating various embodiments of the disclosure and are not meant to limit the present disclosure in any fashion. The present examples, along with the methods described herein are presently representative of preferred embodiments, are exemplary, and are not intended as limitations on the scope of the disclosure. Changes therein and other uses which are encompassed within the spirit of the disclosure as defined by the scope of the claims will occur to those skilled in the art.

Example 1: Gene Expression Studies

This Example shows the effects of the different active agents in gene expression in fibroblasts and keratinocytes.

Methods

Cell Lines. Human adult dermal fibroblast and keratinocyte cell lines were treated with 11 different compound treatments (plus DMSO control as treatment #12). Primary fibroblasts, keratinocytes sourced from ZenBio. Primary cells were plated in cell specific media at 5K or 10K cells per $cm^2$ as per ZenBio instructions. Cells were plated in 48 well plates (Greiner) in triplicate, one cell line per plate. Media volume was 500 ul per well. Outer two columns of wells were not used. All rows were used. Cells were cultured for 2 days in 37° C. 5% $CO_2$ incubator. After 48 hours all the cell cultures were uniform and appeared healthy, no appreciable number of floating dead cells or evidence of vacuolization of cells that might indicate apoptotic or dying cells.

Compounds. Stocks of compounds 1 through 8 on the list below were prepared in PBS at 100× the concentration indicated in red type. A 50 mg/ml stock of compound 9 (PS, phosphatidylserine) was prepared in DMSO but did not fully go into solution with extensive vortexing and warming. This stock was 100× of final concentration. A 20 mg/ml stock of compound 10 (CBD) was prepared in DMSO. No undissolved particulates were observed but the stock solution was slightly cloudy, not completely clear. This stock was 200× of final concentration.

Cell Treatments:

1. Lactoferrin (Lacto)
2. TCVRRAF (SEQ ID NO: 23) (LCV)
3. Tripeptide-1 (Tri)
4. Hexapeptide-12 (Hex12)
5. Tripeptide-1 and Hexapeptide-12 (TriHex)
6. Hexapeptide-11 (Hex11)
7. Tranexamic acid 5% (Tran Acid)
8. Octapeptide (Octa)
9. Phosphatidylserine (Phos)

Dosing. After 48 hours of attachment culture, fibroblasts and keratinocytes were treated with the test compounds. Compounds were resuspended in the appropriate cell media at final concentration in the table below, and the attachment culture media removed and compound containing media added.

RNA Lysate preparation. After 24 hours of compound exposure, the media was removed, the cells were washed 1× with PBS. 100 ul of RNA Lysis Buffer (Takara Bio Cat Num 635013, "10× RNA lysis buffer", diluted to 1×) was added to the well and mixed thoroughly by trituration, combined in RNAse free microcentrifuge tubes and immediately frozen at −30 C. Samples were prepared from one cell line (one plate) at a time. Plate array is 12×4, with each treatment in a row of 3 wells. The triplicate wells were lysed and combined into a tube in a PCR tube strip. All samples were shipped frozen on dry ice to MedGenome for RNA extraction, library construction and sequencing to 25M paired end 100 bp reads per sample.

Sequencing. Library preparation and sequencing was complete at MedGenome.

Results

FIG. 1 shows data of Hyaluronic Acid Synthase 2 (HAS2), which is a primary stimulant of HA in fibroblasts, in fibroblasts treated with the various compounds. Octapeptide showed excellent stimulation of Hyaluronic Acid Synthase 2 (HAS2) (FIG. 1).

Figure 2:
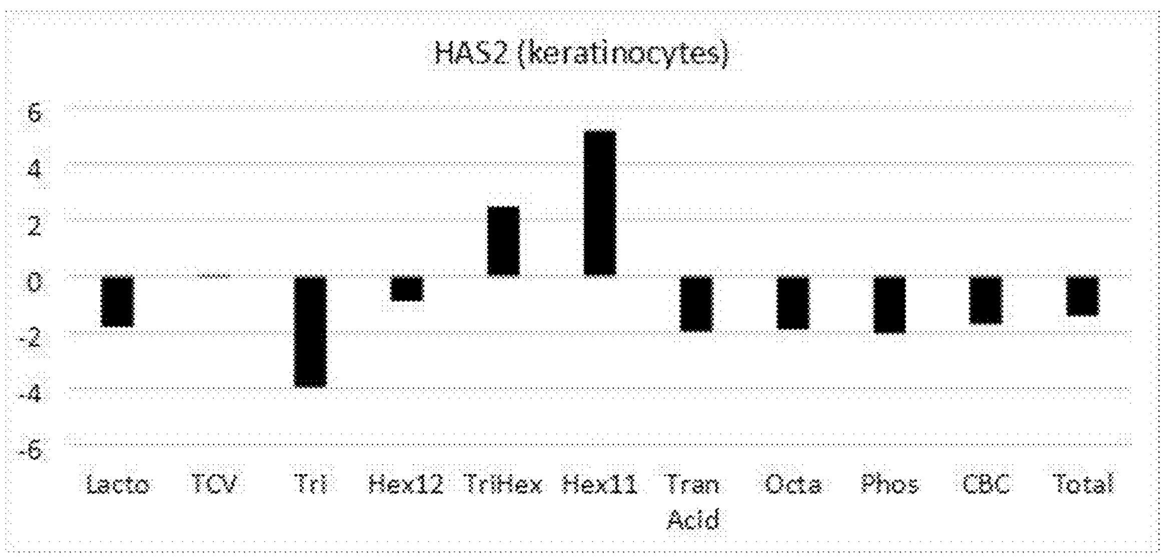
FIG. 2 depicts a graph of Hyaluronic acid Synthase 2 (HAS2) expression in keratinocytes.
Figure 3:
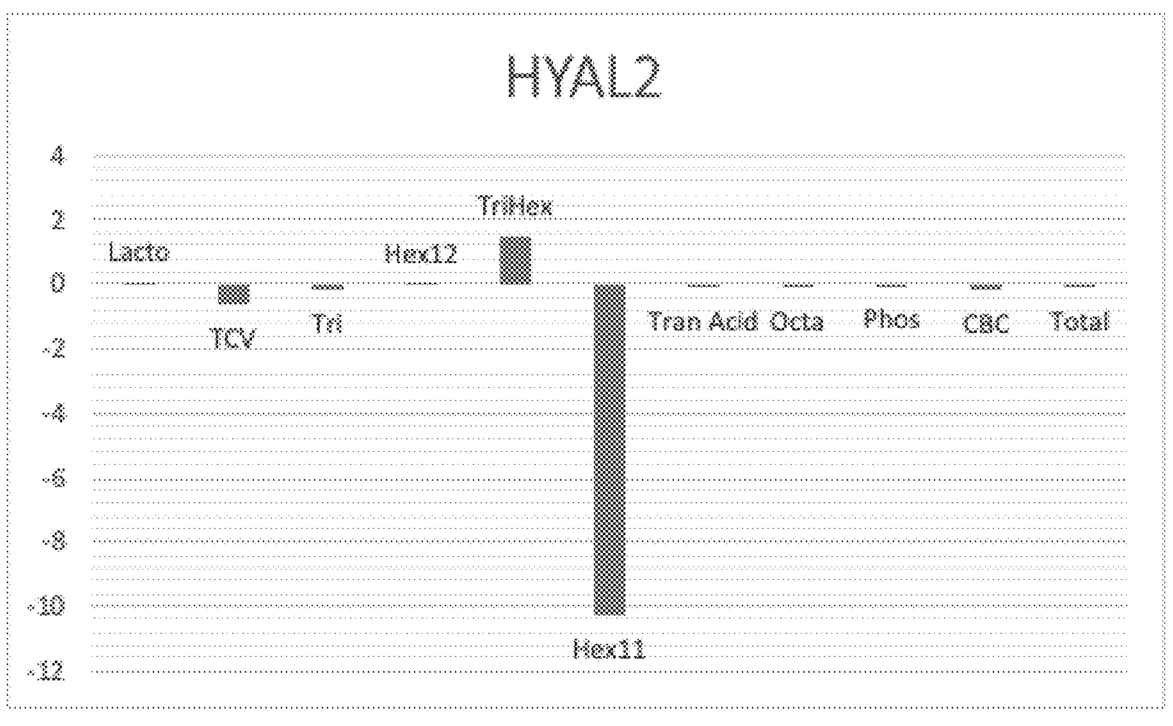
FIG. 3 depicts a graph of Hyaluronidase 2 (HYAL2) expression in keratinocytes.

FIG. 2 shows data of HAS2 in keratinocytes treated with the various compounds. FIG. 3 shows data of Hyaluronidase 2 (HYAL2), which is a HA reducing enzyme, in keratinocytes treated with the various compounds. Hexapeptide-11 showed excellent upregulation of HAS2 in keratinocytes and potent downregulation of HYAL2 in keratinocytes.

This Example shows that the peptides described herein are involved in regulating gene expression of genes involved in hyaluronic acid stimulation.

Example 2: HA Production Assessment

This Example assays whether octapeptide, SymDecanox™ (topical antioxidant), Tremella, lactoferrin, phosphatidylserine, Hylasome™ (sodium hyaluronate crosspolymer), Aquaxyl™ (sugar-derived moisturizing agent) and full formulation stimulate the secretion of high-molecular weight (HMW) hyaluronic acid (HA) from dermal fibroblasts (and keratinocytes). This Example also assays for HA synthesis.

Briefly, dermal fibroblasts and keratinocytes were cultured in growth medium (6-well dishes). When they reached confluence, the growth medium was replaced with serum-free medium for 24 hours. The test agents listed below were added as the experimental treatments.

Test Agents for HA Study (Experiment 1):

1. Octapeptide—10 ug/mL
2. Lactoferrin—500 ug/mL
3. SynHycan—500 ug/mL
4. Phosphatidylserine—500 ug/mL
5. Hylasome™ (sodium hyaluronate crosspolymer)—500 ug/mL
6. Tremella—500 ug/mL
7. SymDecanox™ (topical antioxidant)—250 ug/mL
8. Aquaxyl™ (sugar-derived moisturizing agent)—500 ug/mL
9. Mix of all compounds (12.5% of the above concentrations for each compounds)
10. Mix of all compounds (40% of the above concentrations for each compounds)

Figure 4:
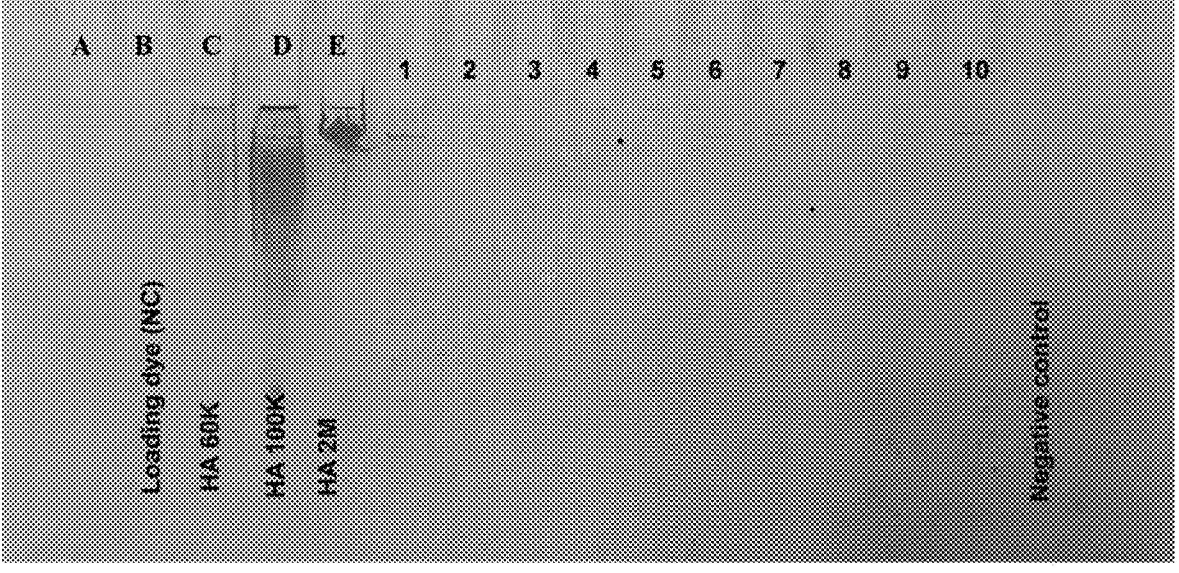
FIG. 4 depicts a SDS-PAGE gel demonstrating the effects of several compounds on hyaluronic acid production in human fibroblast cells 72 hours after treatment in a first experiment.

The supernatants from the cells after the treatments were collected at 24, 48 and 72 hours and aliquoted before storage to prevent freeze-thaw degradation. 60K, 100K and 2 MDa HA were used as reference proteins. SDS-PAGE was used to separate MW sizes from proteins isolated from supernatants along with reference proteins as comparators. The gel was stained with ALL-STAINS to compare molecular weights (MWs). Data is seen in FIG. 4 showing the effect of several compounds on hyaluronic acid production in human fibroblast cells 72 hours after treatment. A, negative control (PBS), B. Loading dye, C. HA marker of 60 k, D. HA marker of 100K, E. HA marker of 2M. Number 1-10 are the name of the compounds listed above. Different MW-HA and HMW-HA at 2M daltons as reference point are shown. FIG. 4 shows fibroblasts producing HA in a range at 2M daltons/HMW HA and none produce HMW-HA.

Figure 5:
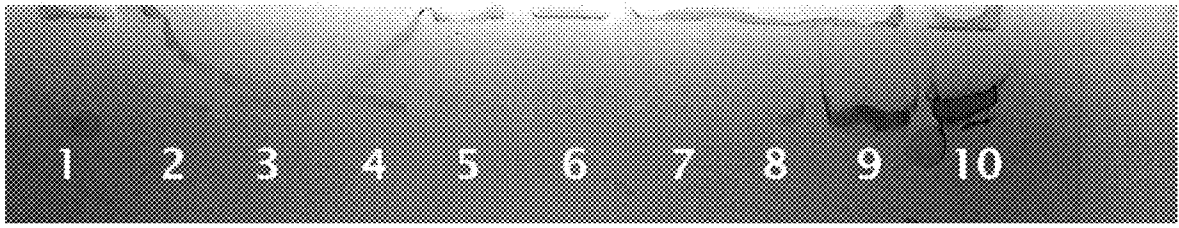
FIG. 5 depicts a SDS-PAGE gel demonstrating effects of octapeptide compounds on hyaluronic acid production in human fibroblast cells 72 hours after treatment in a first experiment.

The effect of octapeptide compounds was also tested on HA production in human fibroblast cells 72 hours after treatment and with the addition of hyaluronidase to confirm disappearance of band. The compounds tested are listed below. Briefly, 100 uL media was harvested from the human fibroblast culture and was concentrated in a SpeedVac concentrator to bring down to 10 uL. Samples were treated with octapeptide with 5 ul of (1 mg/uL) hyaluronidase enzyme for 90 minutes at 37° C. Data is seen in FIG. 5.

Compounds Tested:

1. Loading buffer (negative control)
2. Octapeptide—1 ug/mL
3. Octapeptide—10 ug/mL
4. Octapeptide—100 ug/mL
5. Harvested media
6. Harvested media
7. Octapeptide—100 ug/mL+hyaluronidase enzyme
8. HA 2M+hyaluronidase enzyme control
9. HA 2M (positive control)
10. HA 2M (positive control)

In a second experiment, HA production was also assessed with the test compounds below. Briefly, primary adult human dermal fibroblast cells were cultured until near confluent in 6 well plates. The cells were treated with the compounds and concentrations indicated to the right. After 72 hours, 100 μL of media were collected from each treatment condition and was concentrated in a SpeedVac concentrator to a final volume of ~10 uL.

Test Agents for HA Study (Experiment 2):

1. Octapeptide—100 ug/mL
2. Lactoferrin—500 ug/mL
3. SynHycan—500 ug/mL
4. Phosphatidylserine—500 ug/mL
5. Hylasome™ (sodium hyaluronate crosspolymer)—500 ug/mL
6. Tremella—500 ug/mL
7. SymDecanox™ (topical antioxidant)—250 ug/mL 8. Aquaxyl™ (sugar-derived moisturizing agent)—500 ug/mL
9. Mix of all compounds (12.5% of the above concentrations for each compounds)
10. Mix of all compounds (40% of the above concentrations for each compounds)
11. Negative control (PBS)
12. HA 2M (positive control)

Figure 6:
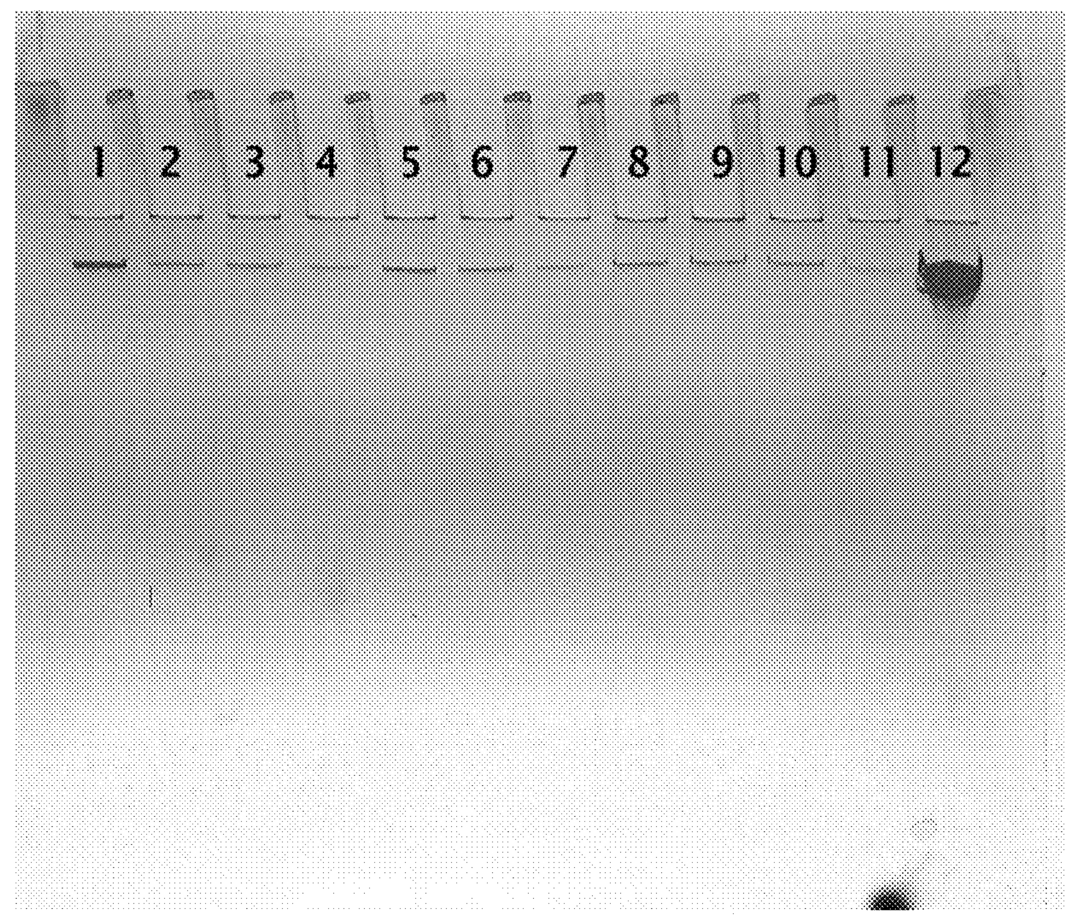
FIG. 6 depicts a SDS-PAGE gel demonstrating the effects of several compounds on hyaluronic acid production in human fibroblast cells 72 hours after treatment in a second experiment.

All 10 μL of the supernatants were loaded onto an acrylamide gel (NuPAGE 4-12% Bis-Tris Protein Gel) and run at 200V for 3 hours. The gel was stained to detect the presence of HA. Data is seen in FIG. 6. Lane 12 is the positive control and shows the size of a band that represents an HA molecule that is 2 MegaDaltons (2M) in size. Lane 11 is the negative control, representing the untreated cells. This band represents the cells constitutive level of HA. Treating the cells with all the indicated compounds (lanes 1-10) produced an increased level of high molecular weight HA. Treatment with Octapeptide alone showed the most intense band.

Figure 7:
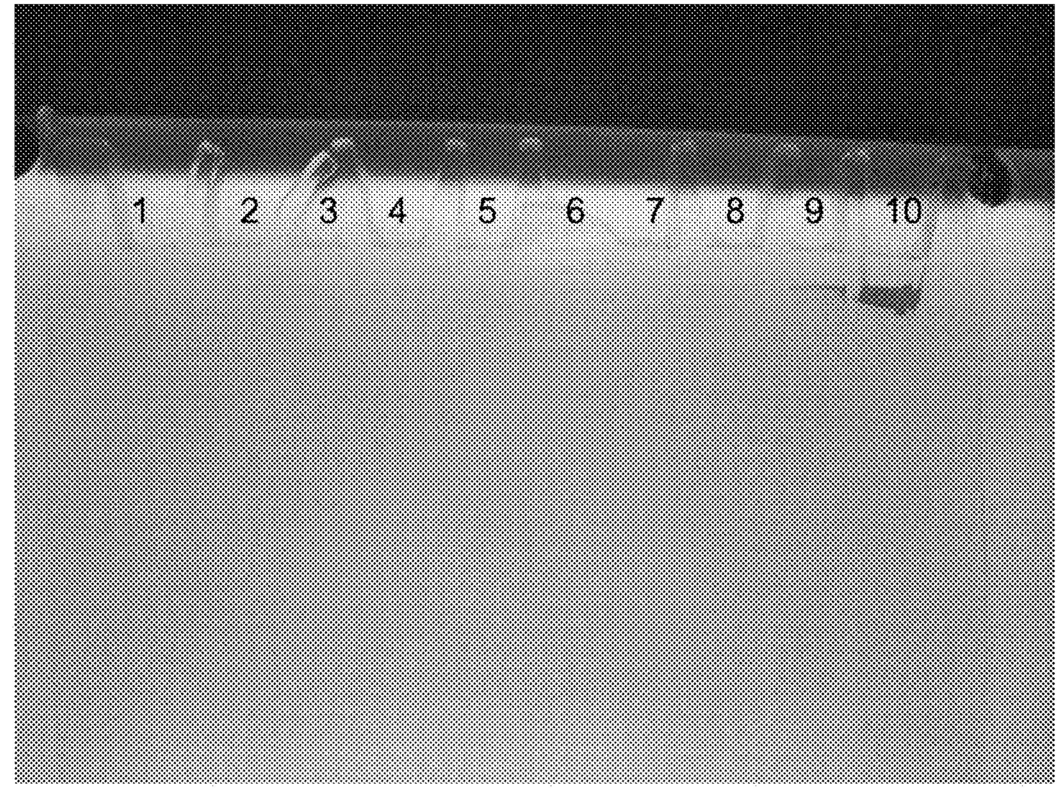
FIG. 7 depicts a SDS-PAGE gel demonstrating the effects of several compounds on hyaluronic acid production in human fibroblast cells 72 hours after treatment in a second experiment.

From the 8 compounds in experiment 2, the supernatants were then digested with hyaluronidase enzyme at 37 for 2 hours (lane 1-8 of FIG. 7). The fact that the band disappeared after the digestion indicates the bands were indeed HA. Lane 9 is the non-digested supernatant after the Octapeptide (100 ug/ml)) treatment. Lane 10 is the positive control with the 2M HA.

Figure 8A:
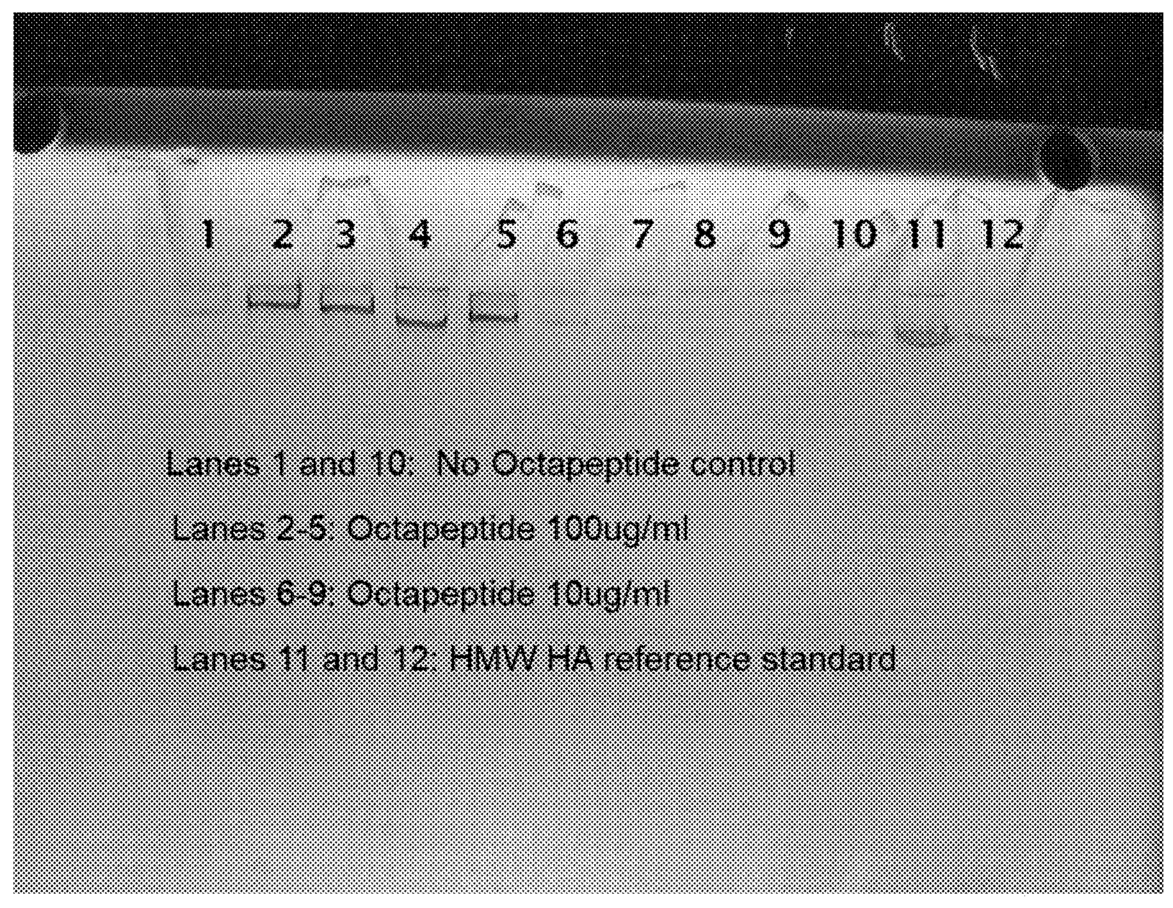
FIGS. 8A-8B depict a SDS-PAGE gel of octapeptide-induced HA production in fibroblast (FIG. 8A) and a graph quantifying the results (FIG. 8B).
Figure 8B:
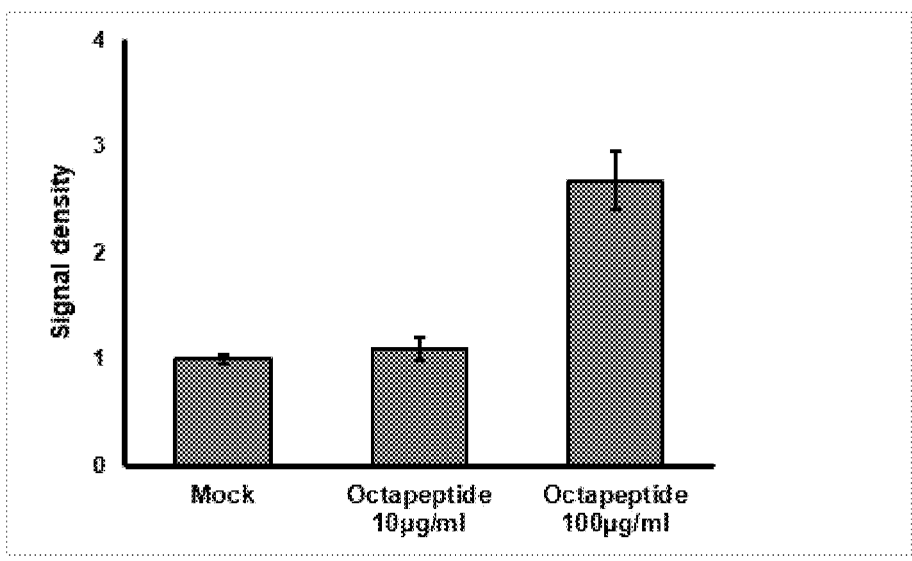
Figure 9:
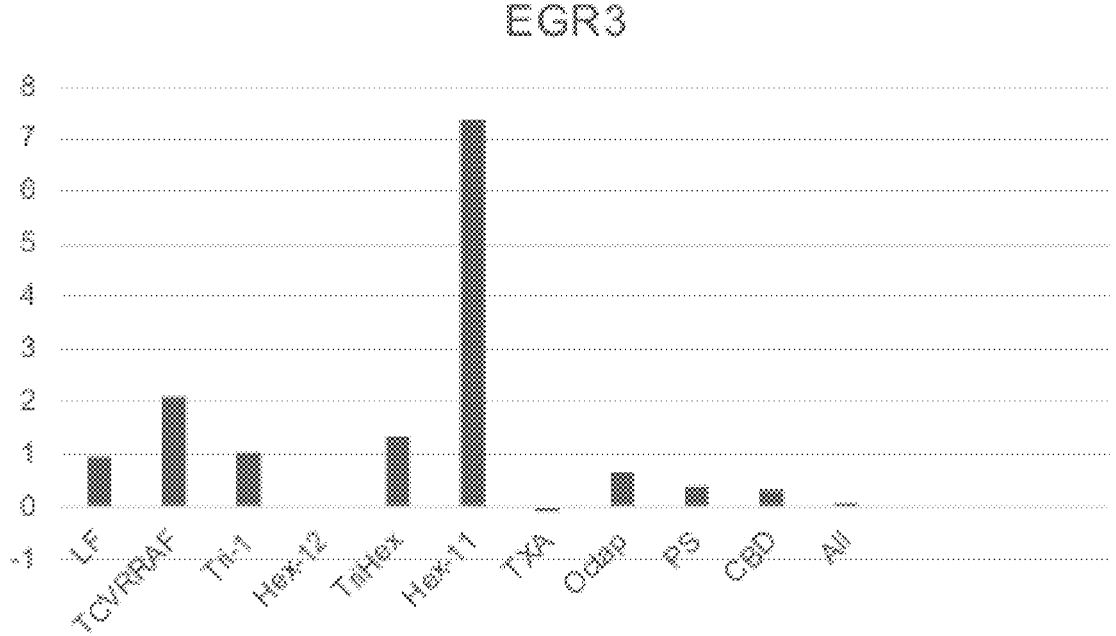
FIG. 9 is a graph demonstrating EGR3 gene expression after treatment with various compounds. The figure discloses "TCVRRAF" (SEQ ID NO: 23).

An experiment was then performed to quantify octapeptide-induced HA production in fibroblasts. Four replicate wells were treated with two concentrations of octapeptide. After 72 hours, the supernatants were collected, concentrated, and run on a gel. A comparison of the replicates in lanes 6-9 and lanes 2-5 indicates that there is dose response for octapeptide-induced HA production (FIG. 8A). The signal intensities were quantified as seen in FIG. 8B.

This Example shows that when fibroblasts are stimulated with Octapeptide, Lactoferrin, SynHycan, Phosphatidylserine, Hylasome™ (sodium hyaluronate crosspolymer), Tremella, SymDecanox™ (topical antioxidant), Aquaxyl™ (sugar-derived moisturizing agent), or a combination of all of these they secrete high molecular weight HA. The presence of HA was validated; after digesting the fibroblast-derived supernatants with hyaluronidase the bands disappeared. Octapeptide alone induced the strongest HA band, which showed a dose-dependent increase. Overall, these compounds are potent stimulators of high molecular weight HA in fibroblasts, particularly octapeptide.

Example 3: EGR3 Gene Studies

This Example assesses EGR3 gene expression. EGR3, a transcription factor specifically present in the granular layer of the epidermis, is the gene that is responsible for the formation of the skin barrier. Selectively increasing EGR3 expression in keratinocytes strengthens the skin barrier.

Briefly, human adult dermal fibroblast and keratinocyte cell lines were treated with 11 different compound treatments. The triplicate wells were lysed and combined into a tube in a

SEQUENCE LISTING

```
Sequence total quantity: 23
SEQ ID NO: 1            moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 1
GDGDGASA                                                                  8

SEQ ID NO: 2            moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 2
GPMGPSGP                                                                  8

SEQ ID NO: 3            moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 3
GLGPGARA                                                                  8

SEQ ID NO: 4            moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 4
GPQGFQGP                                                                  8
```

```
SEQ ID NO: 5            moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 5
GPHGVREA                                                                     8

SEQ ID NO: 6            moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 6
GPMGPRGP                                                                     8

SEQ ID NO: 7            moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 7
GPGKNGDD                                                                     8

SEQ ID NO: 8            moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 8
GPMGPRGP                                                                     8

SEQ ID NO: 9            moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 9
GQPR                                                                         4

SEQ ID NO: 10           moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 10
KTFK                                                                         4

SEQ ID NO: 11           moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 11
AQTR                                                                         4

SEQ ID NO: 12           moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 12
```

```
RSRK                                                        4

SEQ ID NO: 13           moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 13
KDVY                                                        4

SEQ ID NO: 14           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 14
KTTKS                                                       5

SEQ ID NO: 15           moltype = AA  length = 5
FEATURE                 Location/Qualifiers
REGION                  1..5
                        note = Description of Artificial Sequence: Synthetic peptide
VARIANT                 5
                        note = Any amino acid
source                  1..5
                        mol_type = protein
                        organism = synthetic construct
SEQUENCE: 15
YGGFX                                                       5

SEQ ID NO: 16           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 16
KLAAK                                                       5

SEQ ID NO: 17           moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 17
VGVAPG                                                      6

SEQ ID NO: 18           moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 18
GKTTKS                                                      6

SEQ ID NO: 19           moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 19
FVAPFP                                                      6

SEQ ID NO: 20           moltype = AA  length = 7
FEATURE                 Location/Qualifiers
REGION                  1..7
                        note = Description of Artificial Sequence: Synthetic peptide
source                  1..7
```

-continued

```
                         mol_type = protein
                         organism = synthetic construct
SEQUENCE: 20
RGYYLLE                                                                      7

SEQ ID NO: 21            moltype = AA  length = 6
FEATURE                  Location/Qualifiers
REGION                   1..6
                         note = Description of Artificial Sequence: Synthetic peptide
REGION                   1..6
                         note = N-term palmitoyl
source                   1..6
                         mol_type = protein
                         organism = synthetic construct
SEQUENCE: 21
VGVAPG                                                                       6

SEQ ID NO: 22            moltype = AA  length = 6
FEATURE                  Location/Qualifiers
REGION                   1..6
                         note = Description of Artificial Sequence: Synthetic peptide
REGION                   1..6
                         note = N-term myristoyl
source                   1..6
                         mol_type = protein
                         organism = synthetic construct
SEQUENCE: 22
VGVAPG                                                                       6

SEQ ID NO: 23            moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 23
TCVRRAF                                                                      7
```

What we claim is:

1. An octapeptide consisting of the sequence GPHGVREA (SEQ ID NO:5).

2. A composition, comprising:

an octapeptide consisting of the sequence GPHGVREA (SEQ ID NO:5); and a pharmaceutically acceptable carrier.

3. The composition of claim 2, comprising 0.25 ppm to 100 ppm of the octapeptide.

4. The composition of claim 2, comprising 1 ppm to 30 ppm of the octapeptide.

5. The composition of claim 2, further comprising a hexapeptide.

6. The composition of claim 5, wherein the hexapeptide is hexapeptide-12 (SEQ ID NO: 22).

7. The composition of claim 6, comprising 0.25 ppm to 25 ppm of the hexapeptide-12.

8. The composition of claim 5, wherein the hexapeptide is hexapeptide-11 (SEQ ID NO: 19).

9. The composition of claim 2, further comprising a tripeptide.

10. The composition of claim 9, wherein the tripeptide is tripeptide-1 (GHK).

11. The composition of claim 10, comprising 0.25 ppm to 25 ppm of the tripeptide-1.

12. A method for promoting cellular production of hyaluronic acid (HA) in skin comprising human fibroblasts, the method comprising:

administering to the skin an effective amount of an octapeptide consisting of the sequence GPHGVREA (SEQ ID NO:5).

13. The method of claim 12 wherein the octapeptide promotes production of hyaluronic acid synthase 2 (HAS2).

14. The method of claim 12, wherein the hyaluronic acid has a molecular weight of about 2 MDa or greater.

15. The method of claim 12, wherein the octapeptide is administered in a composition comprising 0.25 ppm to 100 ppm of the octapeptide.

16. The method of claim 15, wherein the composition comprises 20 ppm to 100 ppm of the octapeptide.

17. The method of claim 15, wherein the composition further comprises a tripeptide.

18. The method of claim 15, wherein the composition further comprises a hexapeptide.

19. The method of claim 12, wherein administering the octapeptide improves one or more of the following:

skin hydration;

appearance of age spots;

appearance of white pseudoscars;

appearance of an uneven skin tone; or appearance of wrinkles.

20. The method of claim 12, wherein the administering is performed before, during, or after the injection of a filler.

* * * * *